United States Patent [19]
Alizon et al.

[11] Patent Number: 5,858,651
[45] Date of Patent: Jan. 12, 1999

[54] NUCLEOTIDE SEQUENCES OF HUMAN IMMUNODEFICIENCY VIRUS TYPE 2 (HIV-2), PROBES OF HIV-2, AND METHODS OF USING THESE PROBES

[75] Inventors: Marc Alizon, Paris; Luc Montagnier, Le Plessis Robinson; Denise Geutard, Paris, all of France; Francois Clavel, Rockville, Md.; Pierre Sonigo; Mireille Guyader, both of Paris, France

[73] Assignee: Institut Pasteur, Paris, France

[21] Appl. No.: 250,103

[22] Filed: May 26, 1994

Related U.S. Application Data

[63] Continuation of Ser. No. 99,391, Jul. 30, 1993, abandoned, which is a continuation of Ser. No. 752,368, Sep. 3, 1991, abandoned, which is a division of Ser. No. 13,477, Feb. 11, 1987, Pat. No. 5,079,342, which is a continuation-in-part of Ser. No. 3,764, Jan. 16, 1987, Pat. No. 5,051,496, which is a continuation-in-part of Ser. No. 933,184, Nov. 21, 1986, abandoned, which is a continuation-in-part of Ser. No. 916,080, Oct. 6, 1986, abandoned, and a continuation-in-part of Ser. No. 835,228, Mar. 3, 1986, Pat. No. 4,839,288.

[30] Foreign Application Priority Data

| Jan. 22, 1986 | [FR] | France | 8600911 |
| Feb. 6, 1986 | [FR] | France | 8601635 |
| Feb. 13, 1986 | [FR] | France | 8601985 |
| Mar. 18, 1986 | [FR] | France | 8603881 |
| Mar. 24, 1986 | [FR] | France | 8604215 |
| Mar. 28, 1986 | [FR] | France | 8604556 |

[51] Int. Cl.$^6$ .............. C12Q 1/68; C12N 15/11; C12N 15/49
[52] U.S. Cl. .......... 435/6; 536/23.1; 536/23.72
[58] Field of Search .......... 435/5, 6; 536/23.1, 536/23.72; 935/72, 78

[56] References Cited

U.S. PATENT DOCUMENTS 5,306,614  4/1994  Alizon et al. ............... 435/5

OTHER PUBLICATIONS

Lathe, J. Mol. Biol., 183 (1985), pp. 1–12.
Franchini et al, Proc. Natl. Acad. Sci, vol. 86, Apr. 1989, pp. 2433–2437.
Guyader et al, Nature, 326, Apr. 16, 1987, pp. 662–669.
Zagerhy et al, Proc. Natl. Acad. Sci., vol. 85, Aug. 1989, pp. 5941–5945.

*Primary Examiner*—George G. Elliott
*Assistant Examiner*—Terry A. McKelvey
*Attorney, Agent, or Firm*—Finnegan, Henderson, Farabow, Garrett & Dunner, LLP

[57] ABSTRACT

A method for diagnosing an HIV-2 (LAV-II) infection and a kit containing reagents for the same is disclosed. These reagents include cDNA probes which are capable of hybridizing to at least a portion of the genome of HIV-2. In one embodiment, the DNA probes are capable of hybridizing to the entire genome of HIV-2. These reagents also include polypeptides encoded by some of these DNA sequences.

21 Claims, 5 Drawing Sheets

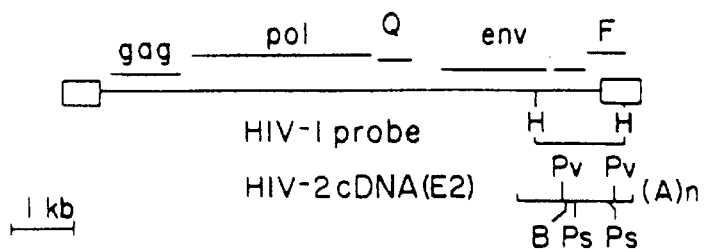

FIG. 2A
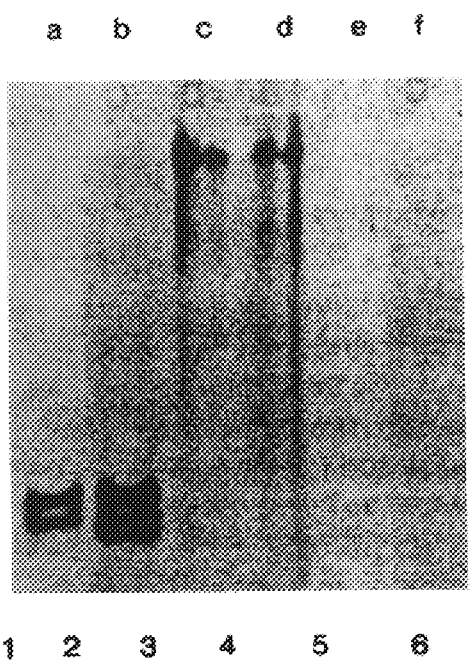
FIG. 2B
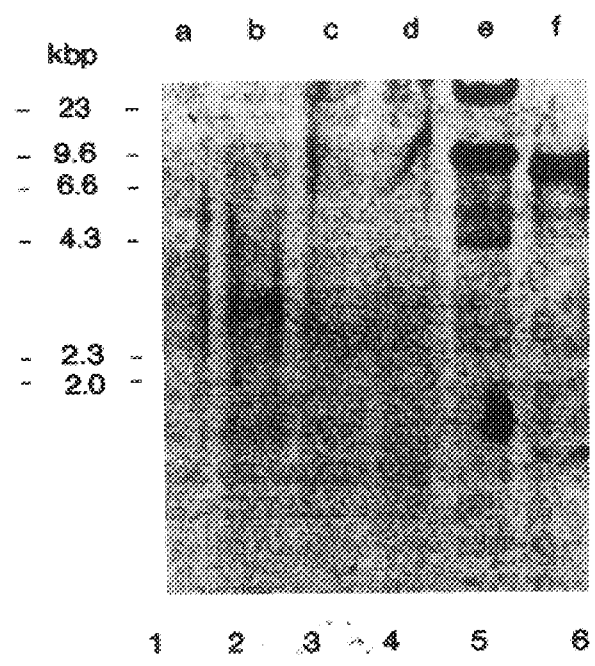
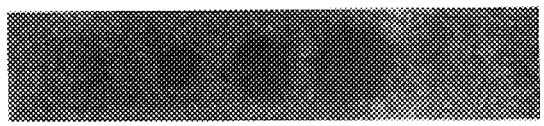
FIG. 2C
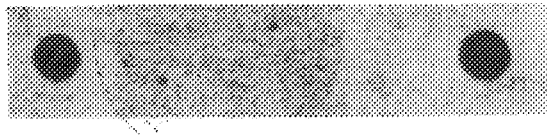
FIG. 2D

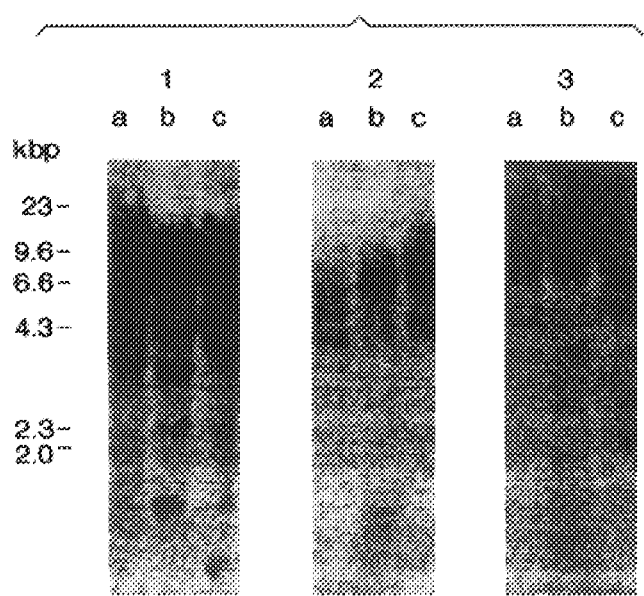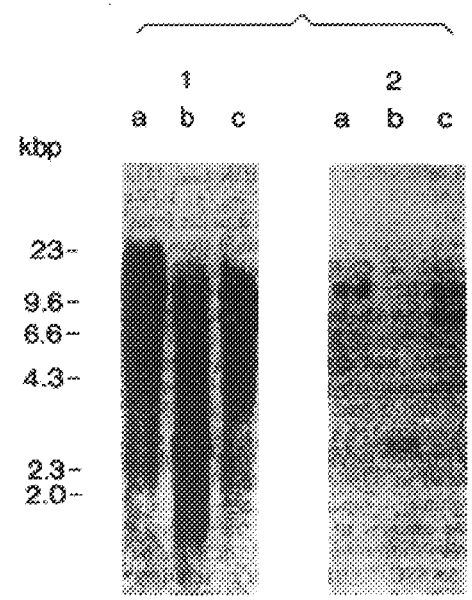

NUCLEOTIDE SEQUENCES OF HUMAN IMMUNODEFICIENCY VIRUS TYPE 2 (HIV-2), PROBES OF HIV-2, AND METHODS OF USING THESE PROBES

This application is a continuation of application Ser. No. 08/099,391, filed Jul. 30, 1993, now abandoned, which is a continuation of application Ser. No. 07/752,368, filed Sep. 3, 1991, now abandoned, which is a divisional of application Ser. No. 07/013,477, filed Feb. 11, 1987, now U.S. Pat. No. 5,079,342, which is a continuation-in-part of application Ser. No. 07/003,764, filed Jan. 16, 1987, now U.S. Pat. No. 5,051,496, which is a continuation-in-part of application Ser. No. 06/933,184, filed Nov. 21, 1986, now abandoned, which is a continuation-in-part application of Ser. No. 06/916,080, filed Oct. 6, 1986, now abandoned and a continuation-in-part of application Ser. No. 06/835,228, filed Mar. 3, 1986, now U.S. Pat. No. 4,839,288.

BACKGROUND OF THE INVENTION

The invention relates to cloned DNA sequences analogous to the genomic RNA of a virus known as Lymphadenopathy-Associated Virus II ("LAV-II"), a process for the preparation of these cloned DNA sequences, and their use as probes in diagnostic kits. In one embodiment, the invention relates to a cloned DNA sequence analogous to the entire genomic RNA of HIV-2 and its use as a probe. The invention also relates to polypeptides with amino acid sequences encoded by these cloned DNA sequences and the use of these polypeptides in diagnostic kits.

According to recently adopted nomenclature, as reported in Nature, May 1986, a substantially-identical group of retroviruses, which has been identified as one causative agent of AIDS are now referred to as Human Immunodeficiency Viruses I (HIV-1). This previously-described group of retroviruses includes Lymphadenopathy-Associated Virus I (LAV-I), Human T-cell Lymphotropic Virus-III (HTLV-III), and AIDS-Related Virus (ARV).

Lymphadenopathy-Associated Virus II has been described in U.S. application Ser. No. 835,228, which was filed Mar. 3, 1986, and is specifically incorporated herein by reference. Because LAV-II is a second, distinct causative agent of AIDS, LAV-II properly is classifiable as a Human Immunodeficiency Virus II (HIV-2). Therefore, "LAV-II" as used hereinafter describes a particular genus of HIV-2 isolates.

While HIV-2 is related to HIV-1 by its morphology, its tropism and its in vitro cytopathic effect on CD4 (T4) positive cell lines and lymphocytes, HIV-2 differs from previously described human retroviruses known to be responsible for AIDS. Moreover, the proteins of HIV-1 and 2 have different sizes and their serological cross-reactivity is restricted mostly to the major core protein, as the envelope glycoproteins of HIV-2 are not immune precipitated by HIV-1-positive sera except in some cases where very faint cross-reactivity can be detected. Since a significant proportion of the HIV infected patients lack antibodies to the major core protein of their infecting virus, it is important to include antigens to both HIV-1 and HIV-2 in an effective serum test for the diagnosis of the infection by these viruses.

HIV-2 was first discovered in the course of serological research on patients native to Guinea-Bissau who exhibited clinical and immunological symptoms of AIDS and from whom sero-negative or weakly sero-positive reactions to tests using an HIV-1 lysate were obtained. Further clinical studies on these patients isolated viruses which were subsequently named "LAV-II."

One LAV-II isolate, subsequently referred to as LAV-II MIR, was deposited at the Collection Nationale des Cultures de Micro-Organismes (CNCM) at the Institut Pasteur in Paris, France on Dec. 19, 1985 under Accession No. I-502 and has also been deposited at the British ECA CC under No. 87.001.001 on Jan. 9, 1987. A second LAV-II isolate was deposited at CNCM on Feb. 21, 1986 under Accession No. I-532 and has also been deposited at the British ECA CC under No. 87.001.002 on Jan. 9, 1987. This second isolate has been subsequently referred to as LAV-II ROD. Other isolates deposited at the CNCM on Dec. 19, 1986 are HIV-2 IRMO (No. I-642) and HIV-2 EHO (No. I-643). Several additional isolates have been obtained from West African patients, some of whom have AIDS, others with AIDS-related conditions and others with no AIDS symptoms. All of these viruses have been isolated on normal human lymphocyte cultures and some of them were thereafter propagated on lymphoid tumor cell lines such as CEM and MOLT.

Due to the sero-negative or weak sero-positive results obtained when using kits designed to identify HIV-1 infections in the diagnosis of these new patients with HIV-2 disease, it has been necessary to devise a new diagnostic kit capable of detecting HIV-2 infection, either by itself or in combination with an HIV-1 infections The present inventors have, through the development of cloned DNA sequences analogous to at least a portion of the genomic RNA of LAV-II ROD viruses, created the materials necessary for the development of such kits.

SUMMARY OF THE INVENTION

As noted previously, the present invention relates to the cloned nucleotide sequences homologous or identical to at least a portion of the genomic RNA of HIV-2 viruses and to polypeptides encoded by the same. The present invention also relates to kits capable of diagnosing an HIV-2 infection.

Thus, a main object of the present invention is to provide a kit capable of diagnosing an infection caused by the HIV-2 virus. This kit may operate by detecting at least a portion of the RNA genome of the HIV-2 virus or the provirus present in the infected cells through hybridization with a DNA probe or it may operate through the immunodiagnostic detection of polypeptides unique to the HIV-2 virus.

Additional objects and advantages of the present invention will be set forth in part in the description which follows, or may be learned from practice of the invention. The objects and advantages may be realized and attained by means of the instrumentalities and combinations particularly pointed out in the appended claims.

To achieve these objects and in accordance with the purposes of the present invention, cloned DNA sequences related to the entire genomic RNA of the LAV-II virus are set forth. These sequences are analogous specifically to the entire genome of the LAV-II ROD strain.

To further achieve the objects and in accordance with the purposes of the present invention, a kit capable of diagnosing an HIV-2 infection is described. This kit, in one embodiment, contains the cloned DNA sequences of this invention which are capable of hybridizing to viral RNA or analogous DNA sequences to indicate the presence of an HIV-2 infection. Different diagnostic techniques can be used which include, but are not limited to: (1) Southern blot procedures to identify viral DNA which may or may not be digested with restriction enzymes; (2) Northern blot techniques to identify viral RNA extracted from cells; and (3) dot blot techniques, i.e., direct filtration of the sample through an ad hoc membrane such as nitrocellulose or nylon without previous separation on agarose gel. Suitable material for dot blot technique could be obtained from body fluids including, but not limited to, serum and plasma, supernatants from culture cells, or cytoplasmic extracts obtained after cell lysis and removal of membranes and nuclei of the cells by ultra-centrifugation as accomplished in the "CYTODOT" procedure as described in a booklet published by Schleicher and Schull.

In an alternate embodiment, the kit contains the polypeptides created using these cloned DNA sequences. These polypeptides are capable of reacting with antibodies to the HIV-2 virus present in sera of infected individuals, thus yielding an immunodiagnostic complex.

In accordance with a further object of the present invention, a peptide is provided as described above, either alone or conjugated to a carrier molecule. This peptide is capable of eliciting the production of an antibody to the peptide, and of forming an effective immunocomplex with the entire HIV-2 retrovirus or with its corresponding proteins.

To further achieve the objects of the invention, a vaccinating agent is provided which comprises at least one peptide selected from the polypeptide expression products of the viral DNA in admixture with suitable carriers, adjuvents stabilizers.

It is understood that both the foregoing general description and the following detailed description are exemplary and explanatory only and are not restrictive of the invention as claimed. The accompanying drawings, which are incorporated in and constitute a part of the specification, illustrate one embodiment of the invention and, together with the description, serve to explain the principles of the invention.

BRIEF DESCRIPTION OF THE DRAWINGS

FIGS. 1A–1B generally depict the nucleotide sequence of a cloned complementary DNA (cDNA) to the genomic RNA of HIV-2. FIG. 1A depicts the genetic organization of HIV-1, position of the HIV-1 HindIII fragment used as a probe to screen the cDNA library, and restriction map of the HIV-2 cDNA clone, E2. FIG. 1B depicts the nucleotide sequence of the 3' end of HIV-2. The corresponding region of the HIV-1 LTR was aligned using the Wilbur and Lipman algorithm (window: 10; K-tuple: 7; gap penalty: 3) as described by Wilbur and Lipman in Proc. Natl. Acad. Sci. USA 80: 726–730 (1983), specifically incorporated herein by reference. The U3-R junction in HIV-1 is indicated and the poly A addition signal and potential TATA promoter regions are boxed. In FIG. 1A, the symbols B, H, Ps and Pv refer to the restriction sites BamHI, HindIII, PstI and PvuII, respectively.

FIGS. 2A–2B generally depict the HIV-2 specificity of the E2 clone. FIG. 2A and B specifically depict a Southern Blot of DNA extracted from CEM cells infected with the following isolates: HIV-$2_{ROD}$ (a,c), HIV-$2_{DUL}$ (b,d), and HIV-$1_{BRU}$ (e,f). DNA in lanes a,b,f was Pst I digested; in c,d,e DNA was undigested. FIG. 2C and D specifically depict dot blot hybridization of pelleted virions from CEM cells infected by the HIV-$1_{BRU}$(1), Simian Immunodeficiency Virus (SIV) isolate Mm 142–83 (3), HIV-$2_{DUL}$ (4), HIV-$2_{ROD}$ (5), and HIV-$1_{ELI}$ (6). Dot 2 is a pellet from an equivalent volume of supernatant from uninfected CEM. Thus, FIG. 2A and C depict hybridization with the HIV-2 cDNA (E2) and FIG. 2B and D depict hybridization to an HIV-1 probe consisting of a 9 Kb SacI insert from HIV-1 BRU(clone lambda J 19).

FIG. 3A specifically depicts the organization of three recombinant phage lambda clones, ROD 4, ROD 27, and ROD 35. In FIG. 3A, the open boxes represent viral sequences, the LTR are filled, and the dotted boxes represent cellular flanking sequences (not mapped). Only some characteristic restriction enzyme sites are indicated. λROD 27 and λROD 35 are derived from integrated proviruses while λROD 4 is derived from a circular viral DNA. The portion of the lambda clones that hybridzes to the cDNA E2 is indicated below the maps. A restriction map of the λROD isolate was reconstructed from these three lambda clones. In this map, the restriction sites are identified as follows: B: BamHI; E: EcoRI; H: HindIII; K: KpnI; Ps: PstI; Pv: PvuII; S: SacI; X: XbaI. R and L are the right and left BamHI arms of the lambda L47.1 vector.

FIG. 3B specifically depicts dots 1–11 which correspond to the single-stranded DNA form of M13 subclones from the HIV-$1_{BRU}$ cloned genome (λJ19). Their size and position on the HIV-1 genome, determined by sequencing is shown below the figure. Dot 12 is a control containing lambda phage DNA. The dot-blot was hybridized in low stringency conditions as described in Example 1 with the complete lambda λROD 4 clone as a probe, and successively washed in 2×SSC, 0.1% SDS at 25° C. (Tm −42° C.), 1×SSC, 0.1% SDS at 60° C. (Tm −20° C.), and 0.1×SSC, 0.1% SDS at 60° C. (Tm −3° C.) and exposed overnight. A duplicate dot blot was hybridized and washed in stringent conditions (as described in Example 2) with the labelled lambda J19 clone carrying the complete HIV-1BRU genome. HIV-1 and HIV-2 probes were labelled the same specific activity ($10^8$ cpm/g.).

FIGS. 4A–4B generally depicts the restriction map polymorphism in different HIV-2 isolates and shows comparison of HIV-2 to SIV. FIG. 4A is a line drawing depicting DNA (20 μg per lane) from CEM cells infected by the isolate HIV-$2_{DUL}$ (panel 1) or peripheral blood lymphocytes (PBL) infected by the isolates HIV-$2_{GOM}$ (panel 2) and HIV-$2_{MIR}$ (panel 3) digested with: EcoRI (a), PstI (b), and HindIII (c). Much less viral DNA was obtained with HIV-2 isolates propagated on PBL. Hybridization and washing were in stringent conditions, as described in Example 2, with $10^6$ cpm/ml. of each of the E2 insert (cDNA) and the 5 kb. HindIII fragment of λROD 4, labelled to $10^9$ cpm/μg.

FIG. 4B is a line drawing depicting depicts DNA from HUT 78 (a human T lymphoid cell line) cells infected with STLV3 MAC isolate Mm 142–83. The same amounts of DNA and enzymes were used as indicated in panel A. Hybridization was performed with the same probe as in A, but in non-stringent conditions. As described in Example 1 washing was for one hour in 2×SSC, 0.1% SDS at 40° C. (panel 1) and after exposure, the same filter was re-washed in 0.1×SSC, 0.1% SDS at 60° C. (panel 2). The autoradiographs were obtained after overnight exposition with intensifying screens.

DETAILED DESCRIPTION OF THE PREFERRED EMBODIMENTS

Figure 3A:
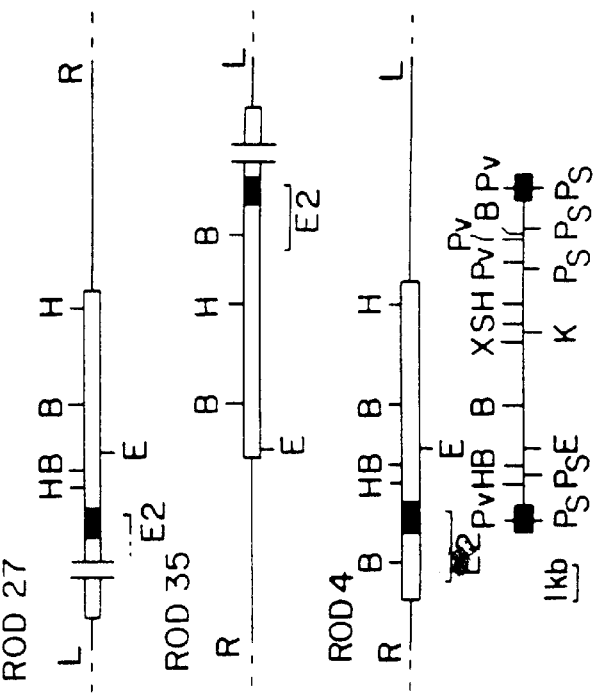
FIGS. 3A–3B generally depict a restriction map of the HIV-2 ROD genome and its homology to HIV-1.

Reference will now be made in detail to the presently preferred embodiments of the invention, which, together with the following examples, serve to explain the principles of the invention.

The genetic structure of the HIV-2 virus has been analyzed by molecular cloning according to the method set forth herein and in the Examples. A restriction map of the genome of this virus is included in FIG. 5. In addition, the partial sequence of a cDNA complementary to the genomic RNA of the virus has been determined. This cDNA sequence information is included in FIG. 1.

Also contained herein is data describing the molecular cloning of the complete 9.5 kb genome of HIV-2, data describing the observation of restriction map polymorphism between different isolates, and an analysis of the relationship between HIV-2 and other human and simian retroviruses. From the totality of these data, diagnostic probes can be discerned and prepared.

Generally, to practice one embodiment of the present invention, a series of filter hybridizations of the HIV-2 RNA genome with probes derived from the complete cloned HIV-1 genome and from the gag and sol genes were conducted. These hybridizations yielded only extremely weak signals even in conditions of very low stringency of hybridization and washing. Thus, it was found to be difficult to assess the amount of HIV-2 viral and proviral DNA in infected cells by Southern blot techniques.

Therefore, a complementary DNA (cDNA) to the HIV-2 genomic RNA initially was cloned in order to provide a specific hybridization probe. To construct this cDNA, an oligo (dT) primed cDNA first-strand was made in a detergent-activated endogenous reaction using HIV-2 reverse transcriptase with virions purified from supernatants of infected CEM cells. The CEM cell line is a lymphoblastoid CD4+ cell line described by G. E. Foley et al. in Cancer 18: 522–529 (1965), specifically incorporated herein by reference. The CEM cells used were infected with the isolate ROD and were continuously producing high amounts of HIV-2.

After second-strand synthesis, the cDNAs were inserted into the M 13 tg 130 bacteriophage vector. A collection of $10^4$ M13 recombinant phages was obtained and screened in situ with an HIV-1 probe spanning 1.5 kb. of the 3' end of the $LAV_{BRU}$ isolate (depicted in FIG. 1A). Some 50 positive plaques were detected, purified, and characterized by end sequencing and cross-hybridizing the inserts. This procedure is described in more detail in Example 1 and in FIG. 1.

The different clones were found to be complementary to the 3' end of a polyadenylated RNA having the AATAAA signal about 20 nucleotides upstream of the poly A tail, as found in the long terminal repeat (LTR) of HIV-1. The LTR region of HIV-1 has been described by S. Wain Hobson et al. in Cell 40: 9–17 (1985), specifically incorporated herein by reference. The portion of the HIV-2 LTR that was sequenced was related only distantly to the homologous domain in HIV-1 as demonstrated in FIG. 1B. Indeed, only about 50% of the nucleotides could be aligned and about a hundred insertions/deletions need to be introduced. In comparison, the homology of the corresponding domains in HIV-1 isolates from USA and Africa is greater than 95% and no insertions or deletions are seen.

The largest insert of this group of M13 clones was a 2 kb. clone designated E2. Clone E2 was used as a probe to demonstrate its HIV-2 specificity in a series of filter hybridization experiments. Firstly, this probe could detect the genomic RNA of HIV-2 but not HIV-1 in stringent conditions as shown in FIG. 2, C and D. Secondly, positive signals were detected in Southern blots of DNA from cells infected with the ROD isolate as well as other isolates of HIV-2 as shown in FIG. 2, A and FIG. 4, A. No signal was detected with DNA from uninfected cells or HIV-1 infected cells, confirming the exogenous nature of HIV-2. In undigested DNA from HIV-2 infected cells, an approximately 10 kb. species, probably corresponding to linear unintegrated viral DNA, was principally detected along with a species with an apparent size of 6 kb., likely to be the circular form of the viral DNA. Conversely, rehybridization of the same filter with an HIV-1 probe under stringent conditions showed hybridization to HIV-1 infected cells only as depicted in FIG. 2, B.

To isolate the remainder of the genome of HIV-2, a genomic library in lambda phage L47.1 was constructed. Lambda phage L47.1 has been described by W. A. M. Loenen et al. in Gene 10: 249–259 (1980), specifically incorporated herein by reference. The genomic library was constructed with a partial Sau3AI restriction digest of the DNA from the CEM cell line infected with HIV-2$_{ROD}$.

About $2 \times 10^6$ recombinant plaques were screened in situ with labelled insert from the E2 cDNA clone. Ten recombinant phages were detected and plaque purified. Of these phages, three were characterized by restriction mapping and Southern blot hybridization with the E2 insert and probes from its 3' end (LTR) or 5' end (envelope), as well as with HIV-1 subgenomic probes. In this instance, HIV-1 probes were used under non-stringent conditions.

Figure 3B:
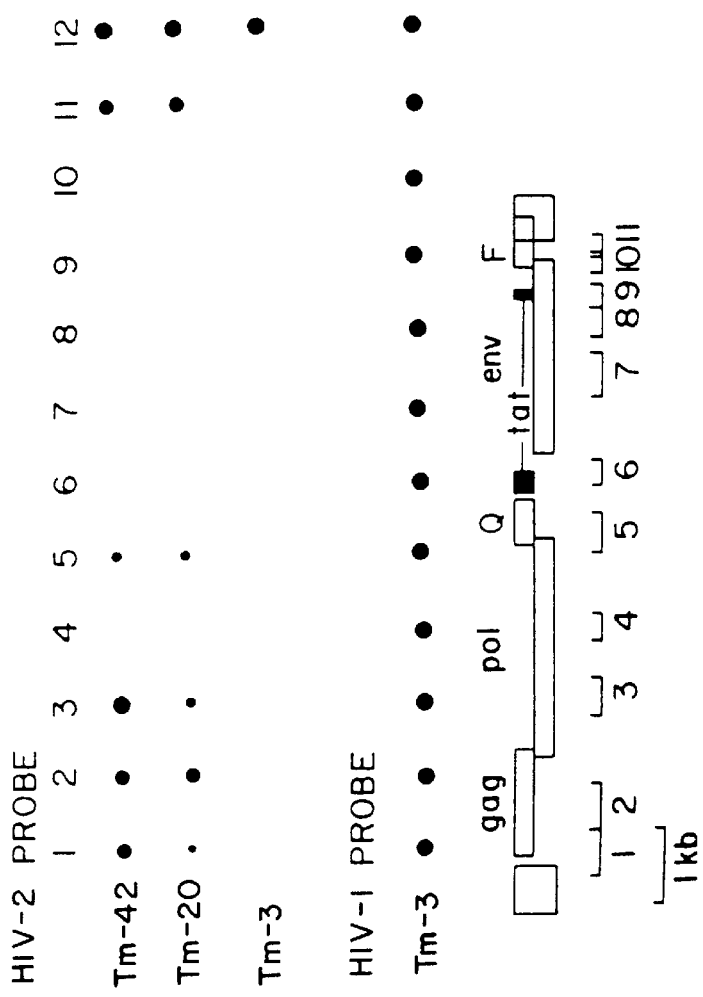

A clone carrying a 9.5 kb. insert and derived from a circular viral DNA was identified as containing the complete genome and designated λROD 4. Two other clones, λROD 27 and λROD 35 were derived from integrated proviruses and found to carry an LTR and cellular flanking sequences and a portion of the viral coding sequences as shown in FIG. 3, A.

Fragments of the lambda clones were subcloned into a plasmid vector p UC 18.

Plasmid pROD 27-5' is derived from λROD 27 and contains the 5' 2Kb of the HIV-2 genome and cellular flanking sequences (5' LTR and 5' viral coding sequences to the EcoRI site)

Plasmid p ROD 4-8 is dervied from λROD 4 and contains the about 5 Kb HindIII fragment that is the central part of the HIV-2 genome.

Plasmid pROD 27-5' and p ROD 4.8 inserts overlap.

Plasmid pROD 4.7 contains a HindIII 1.8 Kb fragment from λROD 4. This fragment is located 3' to the fragment subcloned into pROD 4.8 and contains about 0.8 Kb of viral coding sequences and the part of the lambda phage (λL47.1) left arm located between the BamH1 and HindIII cloning sites.

Plasmid pROD 35 contains all the HIV-2 coding sequences 3' to the EcoRI site, the 3' LTR and about 4 Kb of cellular flanking sequences.

Figure 5:
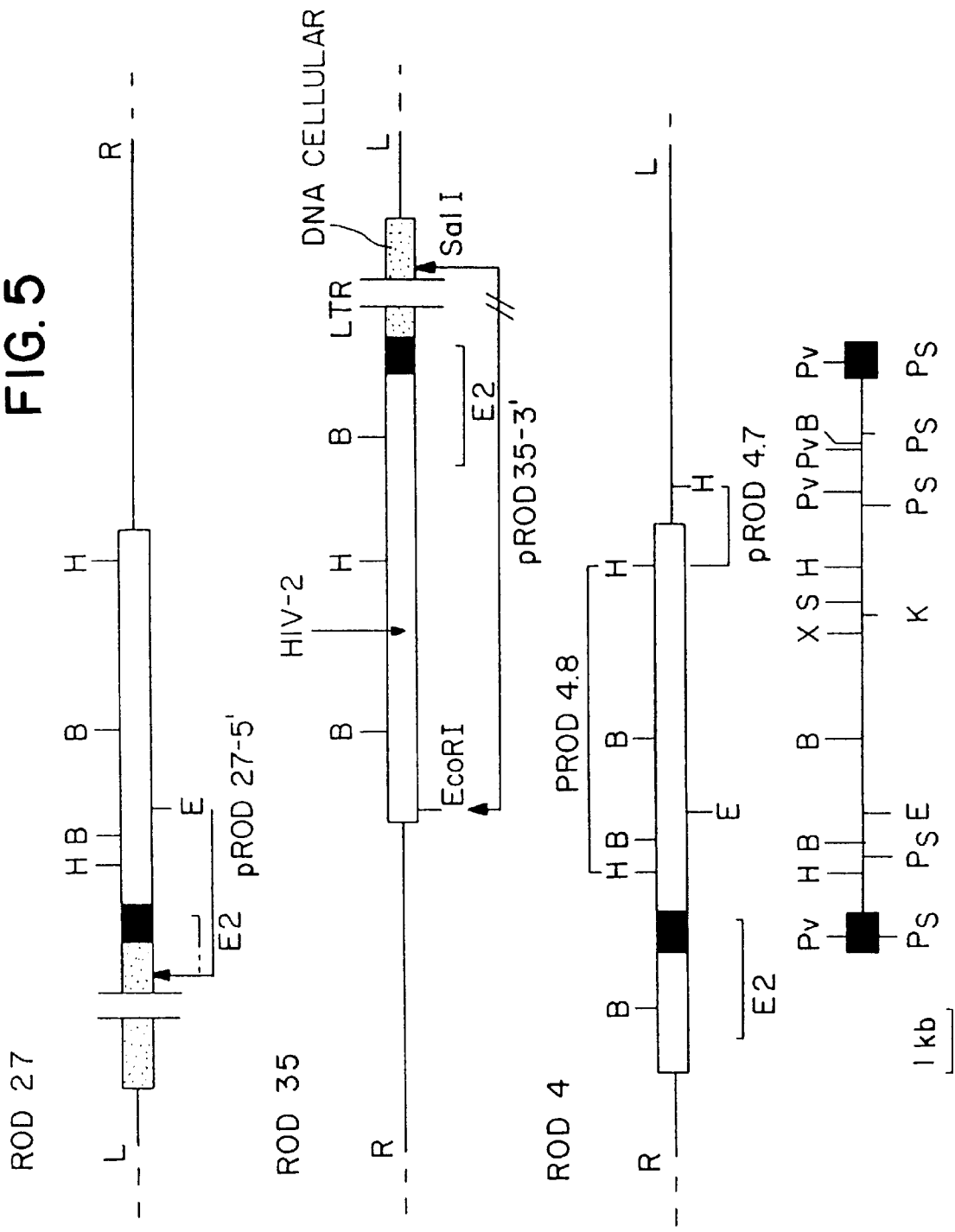
FIG. 5 depicts the position of derived plasmids from λROD 27, λROD 35 and ROD 4.

Plasmid pROD 27-5' and pROD 35 in *E. coli* strain HB 101 are deposited respectively under No. I-626 and I-633 at the CNCM, and have also been deposited at the NCIB (British Collection). These plasmids are depicted in FIG. 5. Plasmids pROD 4-7 and pROD 4-8 in *E. coli* strain TG1 are deposited respectively under No. I-627 and I-628 at the CNCM.

To reconstitute the complete HIV-2 ROD genome, pROD 35 is linearized with EcoRI and the EcoRI insert of pROD 27-5' is ligated in the correct orientation into this site.

The relationship of HIV-2 to other human and simian retroviruses was surmised from hybridization experiments. The relative homology of the different regions of the HIV-1 and 2 genomes was determined by hybridization of fragments of the cloned HIV-1 genome with the labelled λROD 4 expected to contain the complete HIV-2 genome (FIG. 3, B). Even in very low stringency conditions (Tm–42° C.), the hybridization of HIV-1 and 2 was restricted to a fraction of their genomes, principally the gag gene (dots 1 and 2), the reverse transcriptase domain in pol (dot 3), the end of pol and the Q (or sor) genes (dot 5) and the F gene (or 3' orf) and 3' LTR (dot 11). The HIV-1 fragment used to detect the HIV-2 cDNA clones contained the dot 11 subclone, which hybridized well to HIV-2 under non-stringent conditions. Only the signal from dot 5 persisted after stringent washing. The envelope gene, the region of the tat gene and a part of pol thus seemed very divergent. These data, along with the LTR sequence obtained (FIG. 1, B), indicated that HIV-2 is not an envelope variant of HIV-1, as are African isolates from Zaire described by Alizon et al., Cell 40: 63–74 (1986).

It was observed that HIV-2 is related more closely to the Simian Immunodeficiency Virus (SIV) than it is to HIV-1. This correlation has been described by F. Clavel et al. in C.R. Acad. Sci. (Paris) 302: 485–488 (1986) and F. Clavel et al. in Science 233: 343–346 (1986), both of which are specifically incorporated herein by reference. Simian Immunodeficiency Virus (also designated Simian T-cell Lymphotropic Virus Type 3, STLV-3) is a retrovirus first isolated from captive macaques with an AIDS-like disease in the USA. This simian virus has been described by M. D. Daniel et al. in Science 228: 1201–1204 (1985), specifically incorporated herein by reference.

All the SIV proteins, including the envelope, are immune precipitated by sera from HIV-2 infected patients, whereas the serological cross-reactivity of HIV-1 to 2 is restricted to the core proteins. However SIV and HIV-2 can be distinguished by slight differences in the apparent molecular weight of their proteins.

In terms of nucleotide sequence, it also appears that HIV-2 is closely related to SIV. The genomic RNA of SIV can be detected in stringent conditions as shown in FIG. 2, C by HIV-2 probes corresponding to the LTR and 3' end of the genome (E2) or to the gag or pol genes. Under the same conditions, HIV-1 derived probes do not detect the SIV genome as shown in FIG. 2, D.

In Southern blots of DNA from SIV-infected cells, a restriction pattern clearly different from HIV-2$_{ROD}$ and other isolates is seen. All the bands persist after a stringent washing, even though the signal is considerably weakened, indicating a sequence homology throughout the genomes of HIV-2 and SIV. It has recently been shown that baboons and macaques could be infected experimentally by HIV-2, thereby providing an interesting animal model for the study of the HIV infection and its preventive therapy. Indeed, attempts to infect non-human primates with HIV-1 have been successful only in chimpanzees, which are not a convenient model.

From an initial survey of the restriction maps for certain of the HIV-2 isolates obtained according to the methods described herein, it is already apparent that HIV-2, like HIV-1, undergoes restriction site polymorphism. FIG. 4 A depicts examples of such differences for three isolates, all different one from another and from the cloned HIV-2$_{ROD}$. It is very likely that these differences at the nucleotide level are accompanied by variations in the amino-acid sequence of the viral proteins, as evidenced in the case of HIV-1 and described by M. Alizon et al. in Cell 46: 63–74 (1986), specifically incorporated herein by reference. It is also to be expected that the various isolates of HIV-2 will exhibit amino acid heterogeneities. See, for example, Clavel et al., Nature 324 (18): 691–695 (1986), specifically incorporated herein by reference.

Further, the chacterization of HIV-2 will also delineate the domain of the envelope glycoprotein that is responsible for the binding of the surface of the target cells and the subsequent internalization of the virus. This interaction was shown to be mediated by the CD4 molecule itself in the case of HIV-1 and similar studies tend to indicate that HIV-2 uses the same receptor. Thus, although there is wide divergence between the env genes of HIV-1 and 2, small homologous domains of the envelopes of the two HIV could represent a candidate receptor binding site. This site could be used to raise a protective immune response against this group of retroviruses.

From the data discussed herein, certain nucleotide sequences have been identified which are capable of being used as probes in diagnostic methods to obtain the immunological reagents necessary to diagnose an HIV-2 infection. In particular, these sequences may be used as probes in hybridization reactions with the genetic material of infected patients to indicate whether the RNA of the HIV-2 virus is present in these patient's lymphocytes or whether an analogous DNA is present. In this embodiment, the test methods which may be utilized include Northern blots, Southern blots and dot blots. One particular nucleotide sequence which may be useful as a probe is the combination of the 5 kb. HindIII fragment of ROD 4 and the E2 cDNA used in FIG. 4.

In addition, the genetic sequences of the HIV-2 virus may be used to create the polypeptides encoded by these sequences. Specifically, these polypeptides may be created by expression of the cDNA obtained according to the teachings herein in hosts such as bacteria, yeast or animal cells. These polypeptides may be used in diagnostic tests such as immunofluorescence assays (IFA), radioimmunoassays (RIA) and Western Blot tests.

Moreover, it is also contemplated that additional diagnostic tests, including additional immunodiagnostic tests, may be developed in which the DNA probes or the polypeptides of this invention may serve as one of the diagnostic reagents. The invention described herein includes these additional test methods.

In addition, monoclonal antibodies to these polypeptides or fragments thereof may be created. The monoclonal antibodies may be used in immunodiagnostic tests in an analogous manner as the polypeptides described above.

The polypeptides of the present invention may also be used as immunogenic reagents to induce protection against infection by HIV-2 viruses. In this embodiment, the polypeptides produced by recombinant-DNA techniques would function as vaccine agents.

Also, the polypeptides of this invention may be used in competitive assays to test the ability of various antiviral agents to determine their ability to prevent the virus from fixing on its target.

Thus, it is to be understood that application of the teachings of the present invention to a specific problem or environment will be within the capabilities of one having ordinary skill in the art in light of the teachings contained herein. Examples of the products of the present invention and representative processes for their isolation and manufacture appear above and in the following examples.

EXAMPLES

Example 1

Cloning of a cDNA Complementary to Genomic RNA From HIV-2 Virions

HIV-2 virions were purified from 5 liters of supernatant from a culture of the CEM cell line infected with the ROD isolate and a cDNA first strand using oligo (dT) primer was synthesized in detergent activated endogenous reaction on pelleted virus, as described by M. Alizon et al. in Nature, 312: 757–760 (1984), specifically incorporated herein by reference. RNA-cDNA hybrids were purified by phenol-chloroform extraction and ethanol precipitation. The second-strand cDNA was created by the DNA polymerase I/RNAase H method of Gubler and Hoffman in Gene, 25: 263–269 (1983), specifically incorporated herein by reference, using a commercial cDNA synthesis kit obtained from Amersham. After attachment of EcoRI linkers (obtained from Pharmacia), EcoRI digestion, and ligation into EcoRI-digested dephosphorylated M13 tg 130 vector (obtained from Amersham), a cDNA library was obtained by transformation of the *E. coli* TG1 strain. Recombinant plaques ($10^4$) were screened in situ on replica filters with the 1.5 kb. HindIII fragment from clone J19, corresponding to the 3' part of the genome of the $LAV_{BRU}$ isolate of HIV-1, $^{32}P$ labelled to a specific activity of $10^9$ cpm/µg. The filters were prehybridized in 5×SSC, 5×Denhardt solution, 25% formamide, and denatured salmon sperm DNA (100 µg/ml) at 37° C. for 4 hours and hybridized for 16 hours in the same buffer (Tm −42° C.) plus $4×10^7$ µcpm of the labelled probe ($10^6$ cpm/ml. of hybridization buffer). The washing was done in 5×SSC, 0.1% SDS at 25° C. for 2 hours. 20×SSC is 3M NaCl, 0.3M Na citrate. Positive plaques were purified and single-stranded M13 DNA prepared and end-sequenced according to the method described in Proc. Nat'l. Acad. Sci. USA, 74: 5463–5467 (1977) of Sanger et al.

Example 2

Hybridization of DNA from HIV-1 and HIV-2 Infected Cells and RNA from HIV-1 and 2 and SIV Virons With a Probe Derived From an HIV-2 Cloned cDNA DNA was extracted from infected CEM cells continuously producing HIV-1 or 2. The DNA digested with 20 µg of PstI or undigested, was electrophoresed on a 0.8% agarose gel, and Southern-transferred to nylon membrane. Virion dot-blots were prepared in duplicate, as described by F. Clavel et al. in Science 233: 343–346 (1986), specifically incorporated herein by reference, by pelleting volumes of supernatant corresponding to the same amount of reverse transcriptase activity. Prehybridization was done in 50% formamide, 5×SSC, 5×Denhardt solution, and 100 mg./ml. denatured salmon sperm DNA for 4 hours at 42° C. Hybridization was performed in the same buffer plus 10% Dextran sulphate, and $10^6$ cpm/ml. of the labelled E2 insert (specific activity $10^9$ cpm/µg.) for 16 hours at 42° C. Washing was in 0.1×SSC, 0.1% SDS for 2×30 mn. After exposition for 16 hours with intensifying screens, the Southern blot was dehybridized in 0.4N NaOH, neutralized, and rehybridized in the same conditions to the HIV-1 probe labelled to $10^9$ cpm/µg.

Example 3

Cloning in Lambda Phage of the Complete Provirus DNA of HIV-2

DNA from the HIV-$2_{ROD}$ infected CEM (FIG. 2, lanes a and c) was partially digested with Sau3AI. The 9–15 kb. fraction was selected on a 5–40% sucrose gradient and ligated to BamHI arms of the lambda L47.1 vector. Plaques ($2×10^6$) obtained after in vitro packaging and plating on *E. coli* LA 101 strain were screened in situ with the insert from the E2 cDNA clone. Approximately 10 positive clones were plaque purified and propagated on *E. coli* C600 recBC. The ROD 4, 27, and 35 clones were amplified and their DNA characterized by restriction mapping and Southern blotting with the HIV-2 cDNA clone under stringent conditions, and gag-pol probes from HIV-1 used under non stringent conditions.

Example 4

Complete Genomic Sequence of the ROD HIV-2 Isolate

Experimental analysis of the HIV-$2_{ROD}$ isolate yielded the following sequence which represents the complete genome of this HIV-2 isolate. Genes and major expression products identified within the following sequence are indicated by nucleotides numbered below:

1) GAG gene (546–2111) expresses a protein product having a molecular weight of around 55 Kd and is cleaved into the following proteins:
   a) p 16 (546–950)
   b) p 26 (951–1640)
   c) p 12 (1701–2111)
2) polymerase (1829–4936)
3) Q protein (4869–5513)
4) R protein (5682–5996)
5) X protein (5344–5679)
6) Y protein (5682–5996)
7) Env protein (6147–8720)
8) F protein (8557–9324)
9) TAT gene (5845–6140 and 8307–8400) is expressed by two exons separated by introns.
10) ART protein (6071–6140 and 8307–8536) is similarly the expression product of two exons.
11) LTR:R (1–173 and 9498–9671)
12) U5 (174–299)
13) U3 (8942–9497)

It will be known to one of skill in the art that the absolute numbering which has been adopted is not essential. For example, the nucleotide within the LTR which is designated as "1" is a somewhat arbitrary choice. What is important is the sequence information provided.

```
GGTCGCTCTGCGGAGAGGCTGGCAGATTGAGCCCTGGGAGGTTCTCTCCAGCACTAGCAG
         *         *         *         *         *         *
GTAGAGCCTGGGTGTTCCCTGCTAGACTCTCACCAGCACTTGGCCGGTGCTGGGCAGACG
                                  100
         *         *         *         *         *         *
GCCCCACGCTTGCTTGCTTAAAAACCTCTTAATAAAGCTGCCAGTTAGAAGCAAGTTAAG
         *         *         *         *         *         *
TGTGTGCTCCCATCTCTCCTAGTCGCCGCCTGGTCATTCGGTGTTCACCTGAGTAACAAG
                                  200
         *         *         *         *         *         *
ACCCTGGTCTGTTAGGACCCTTCTTGCTTTGGGAAACCGAGGCAGGAAAATCCCTAGCAG
                                                              300
```

-continued

```
GTTGGCGCCTGAACAGGGACTTGAAGAAGACTGAGAAGTCTTGGAACACGGCTGAGTGAA

GGCAGTAAGGGCGGCAGGAACAAACCACGACGGAGTGCTCCTAGAAAGGCGCGGGCCGAG
                                          400
GTACCAAAGGCAGCGTGTGGAGCGGGAGGAGAAGAGGCCTCCGGGTGAAGGTAAGTACCT

ACACCAAAAACTGTAGCCGAAAGGGCTTGCTATCCTACCTTTAGACAGGTAGAAGATTGT
                 500
         Met Gly Ala Arg Asn Ser Val Leu Arg Gly Lys Lys Ala Asp Glu Leu Glu Arg Ile
GGGAGATGGGCGCGAGAAACTCCGTCTTGAGAGGGAAAAAAGCAGATGAATTAGAAAGAA
                                                                  600
 Arg Leu Arg Pro Gly Gly Lys Lys Lys Tyr Arg Leu Lys His Ile Val Trp Ala Ala Asn
TCAGGTTACGGCCCGGCGGAAAGAAAAAGTACAGGCTAAAACATATTGTGTGGGCAGCGA
 Lys Leu Asp Arg Phe Gly Leu Ala Glu Ser Leu Leu Glu Ser Lys Glu Gly Cys Gln Lys
ATAAATTGGACAGATTCGGATTAGCAGAGAGCCTGTTGGAGTCAAAAGAGGGTTGTCAAA
                                                   700
 Ile Leu Thr Val Leu Asp Pro Met Val Pro Thr Gly Ser Glu Asn Leu Lys Ser Leu Phe
AAATTCTTACAGTTTTAGATCCAATGGTACCGACAGGTTCAGAAAATTTAAAAAGTCTTT
 Asn Thr Val Cys Val Ile Trp Cys Ile His Ala Glu Glu Lys Val Lys Asp Thr Glu Gly
TTAATACTGTCTGCGTCATTTGGTGCATACACGCAGAAGAGAAAGTGAAAGATACTGAAG
                       800
     Ala Lys Gln Ile Val Arg Arg His Leu Val Ala Glu Thr Gly Thr Ala Glu Lys Met Pro
GAGCAAAACAAATAGTGCGGAGACATCTAGTGGCAGAAACAGGAACTGCAGAGAAAATGC
                                                                  900
 Ser Thr Ser Arg Pro Thr Ala Pro Ser Ser Glu Lys Gly Gly Asn Tyr Pro Val Gln His
CAAGCACAAGTAGACCAACAGCACCATCTAGCGAGAAGGGAGGAAATTACCCAGTGCAAC
 Val Gly Gly Asn Tyr Thr His Ile Pro Leu Ser Pro Arg Thr Leu Asn Ala Trp Val Lys
ATGTAGGCGGCAACTACACCCATATACCGCTGAGTCCCCGAACCCTAAATGCCTGGGTAA
                                          1000
 Leu Val Glu Glu Lys Lys Phe Gly Ala Glu Val Val Pro Gly Phe Ile Ala Leu Ser Glu
AATTAGTAGAGGAAAAAAAGTTCGGGGCAGAAGTAGTGCCAGGATTTCAGGCACTCTCAG
 Gly Cys Thr Pro Tyr Asp Ile Asn Gln Met Leu Asn Cys Val Gly Asp His Gln Ala Ala
AAGGCTGCACGCCCTATGATATCAACCAAATGGTTAATTGTGTGGGCGACCATCAAGCAG
                          1100
 Met Gln Ile Ile Arg Glu Ile Ile Asn Glu Glu Ala Ala Glu Trp Asp Val Gln Lis Pro
CCATGCAGATAATCAGGGAGATTATCAATGAGGAAGCAGCAGAATGGGATGTGCAACATC
                                                                  1200
 Ile Pro Gly Pro Leu Pro Ala Gly Gln Leu Arg Glu Pro Arg Gly Ser Asp Ile Ala Gly
CAATACCAGGCCCCTTACCAGCGGGGCAGCTTAGAGAGCCAAGGGGATCTGACATAGCAG
 Thr Thr Ser Thr Val Glu Glu Gln Ile Gln Trp Met Phe Arg Pro Gln Asn Pro Val Pro
GGACAACAAGCACAGTAGAAGAACAGATCCAGTGGATGTTTAGGCCACAAAATCCTGTAC
                                                   1300
 Val Gly Asn Ile Tyr Arg Arg Trp Ile Gln Ile Gly Leu Gln Lys Cys Val Arg Met Tyr
CAGTAGGAAACATCTATAGAAGATGGATCCAGATAGGATTGCAGAAGTGTGTCAGGATGT
 Asn Pro Thr Asn Ile Leu Asp Ile Lys Gln Gly Pro Lys Glu Pro Phe Gln Ser Tyr Val
ACAACCCGACCAACATCCTAGACATAAAACAGGGACCAAAGGAGCCGTTCCAAAGCTATG
                 1400
 Asp Arg Phe Tyr Lys Ser Leu Arg Ala Glu Gln Thr Asp Pro Ala Val Lys Asn Trp Met
TAGATAGATTCTACAAAAGCTTGAGGGCAGAACAAACAGATCCAGCAGTGAAGAATTGGA
                                                                  1500
 Thr Gln Thr Leu Leu Val Gln Asn Ala Asn Pro Asp Cys Lys Leu Val Leu Lys Gly Leu
TGACCCAAACACTGCTAGTACAAAATGCCAACCCAGACTGTAAATTAGTGCTAAAAGGAC
 Gly Met Asn Pro Thr Leu Glu Glu Met Leu Thr Ala Cys Gln Gly Val Gly Gly Pro Gly
TAGGGATGAACCCTACCTTAGAAGAGATGCTGACCGCCTGTCAGGGGGTAGGTGGGCCAG
                                          1600
 Gln Lys Ala Arg Leu Met Ala Glu Ala Leu Lys Glu Val Ile Gly Pro Ala Pro Ile Pro
GCCAGAAAGCTAGATTAATGGCAGAGGCCCTGAAAGAGGTCATAGGACCTGCCCCTATCC
 Phe Ala Ala Ala Gln Gln Arg Lys Ala Phe Lys Cys Trp Asn Cys Gly Lys Glu Gly His
CATTCGCAGCAGCCCAGCAGAGAAAGGCATTTAAATGCTGGAACTGTGGAAAGGAAGGGC
                 1700
 Ser Ala Arg Gln Cys Arg Ala Pro Arg Arg Gln Gly Cys Trp Lys Cys Gly Lys Pro Gly
ACTCGGCAAGACAATGCCGAGCACCTAGAAGGCAGGGCTGCTGGAAGTGTGGTAAGCCAG
                                                                  1800
                             Thr Gly Arg Phe Phe Arg Thr Gly Pro Leu Gly
     His Ile Met Thr Asn Cys Pro Asp Arg Gln Ala Gly Phe Leu Gly Leu Gly Pro Trp Gly
GACACATCATGACAAACTGCCCAGATAGACAGGCAGGTTTTTTAGGACTGGGCCCTTGGG
```

-continued

```
          *                   *                   *                   *                   *                   *
Lys Glu Ala Pro Gln Leu Pro Arg Gly Pro Ser Ser Ala Gly Ala Asp Thr Asn Ser Thr
Lys Lys Pro Arg Asn Phe Pro Val Ala Gln Val Pro Gln Gly Leu Thr Pro Pro Thr Pro
GAAAGAAGCCCCGCAACTTCCCCGTGGCCCAAGTTCCGCAGGGGCTGACACCAACAGCAC
                                                            1900
          *                   *                   *                   *                   *                   *
Pro Ser Gly Ser Ser Ser Gly Ser Thr Gly Glu Ile Tyr Ala Ala Arg Glu Lys Thr Glu
Pro Val Asp Pro Ala Val Asp Leu Leu Glu Lys Tyr Met Gln Gln Gly Lys Arg Gln Arg
CCCCAGTGGATCCAGCAGTGGATCTACTGGAGAAATATATGCAGCAAGGGAAAAGACAGA
          *                   *                   *                   *                   *                   *
Arg Ala Glu Arg Glu Thr Ile Gln Gly Ser Asp Arg Gly Leu Thr Ala Pro Arg Ala Gly
Glu Gln Arg Glu Arg Pro Tyr Lys Glu Val Thr Glu Asp Leu Leu His Leu Glu Gln Gly
GAGAGCAGAGAGAGAGACCATACAAGGAAGTGACAGAGGACTTACTGCACCTCGAGCAGG
                              2000
          *                   *                   *                   *                   *                   *
Gly Asp Thr Ile Gln Gly Ala Thr Asn Arg Gly Leu Ala Ala Pro Gln Phe Ser Leu Trp
Glu Thr Pro Tyr Arg Glu Pro Pro Thr Glu Asp Leu Leu His Leu Asn Ser Leu Phe Gly
GGGAGACACCATACAGGGAGCCACCAACAGAGGACTTGCTGCACCTCAATTCTCTCTTTG
                                                                                                  2100
              *                   *                   *                   *                   *
Lys Arg Pro Val Val Thr Ala Tyr Ile Glu Gly Gln Pro Val Glu Val Leu Leu Asp Thr
Lys Asp Gln
GAAAAGACCAGTAGTCACAGCATACATTGAGGGTCAGCCAGTAGAAGTCTTGTTAGACAC
          *                   *                   *                   *                   *                   *
Gly Ala Asp Asp Ser Ile Val Ala Gly Ile Glu Leu Gly Lys Asn Asn Tyr Ser Pro Lys Ile
AGGGGCTGACGACTCAATAGTAGCAGGAATAGAGTTAGGGAACAATTATAGCCCAAAAAT
                                        2200
          *                   *                   *                   *                   *                   *
Val Gly Gly Ile Gly Gly Phe Ile Asn Thr Lys Glu Tyr Lys Asn Val Glu Ile Glu Val
AGTAGGGGGAATAGGGGGATTCATAAATACCAAGGAATATAAAAATGTAGAAATAGAAGT
          *                   *                   *                   *                   *                   *
Leu Asn Lys Lys Val Arg Ala Thr Ile Met Thr Gly Asp Thr Pro Ile Asn Ile Phe Gly
TCTAAATAAAAAGGTACGGGCCACCATAATGACAGGCGACACCCCAATCAACATTTTTGG
                        2300
          *                   *                   *                   *                   *
Arg Asn Ile Leu Thr Ala Leu Gly Met Ser Leu Asn Leu Pro Val Ala Lys Val Glu Pro
CAGAAATATTCTGACAGCCTTAGGCATGTCATTAAATCTACCAGTCGCCAAAGTAGAGCC
                                                                                                  2400
          *                   *                   *                   *                   *
Ile Lys Ile Met Leu Lys Pro Gly Lys Asp Gly Pro Lys Leu Arg Gln Trp Pro Leu Thr
AATAAAAATAATGCTAAAGCCAGGGAAAGATGGACCAAAACTGAGACAATGGCCCTTAAC
          *                   *                   *                   *                   *                   *
Lys Glu Lys Ile Glu Ala Leu Lys Glu Ile Cys Glu Lys Met Glu Lys Glu Gly Gln Leu
AAAAGAAAAAATAGAAGCACTAAAAGAAATCTGTGAAAAAATGGAAAAAGAAGGCCAGCT
                                        2500
          *                   *                   *                   *                   *                   *
Glu Glu Ala Pro Pro Thr Asn Pro Tyr Asn Thr Pro Thr Phe Ala Ile Lys Lys Lys Asp
AGAGGAAGCACCTCCAACTAATCCTTATAATACCCCCACATTTGCAATCAAGAAAAAGGA
          *                   *                   *                   *                   *                   *
Lys Asn Lys Trp Arg Met Leu Ile Asp Phe Arg Glu Leu Asn Lys Val Thr Gln Asp Phe
CAAAAACAAATGGAGGATGCTAATAGATTTCAGAGAACTAAACAAGGTAACTCAAGATTT
                              2600
          *                   *                   *                   *                   *
Thr Glu Ile Gln Leu Gly Ile Pro His Pro Ala Gly Leu Ala Lys Lys Arg Arg Ile Thr
CACAGAAATTCAGTTAGGAATTCCACACCCAGCAGGGTTGGCCAAGAAGAGAAGAATTAC
                                                                                                  2700
          *                   *                   *                   *                   *
Val Leu Asp Val Gly Asp Ala Tyr Phe Ser Ile Pro Leu His Glu Asp Phe Arg Pro Tyr
TGTACTAGATGTAGGGGATGCTTACTTTTCCATACCACTACATGAGGACTTTAGACCATA
          *                   *                   *                   *                   *                   *
Thr Ala Phe Thr Leu Pro Ser Val Asn Asn Ala Glu Pro Gly Lys Arg Tyr Ile Tyr Lys
TACTGCATTTACTCTACCATCAGTGAACAATGCAGAACCAGGAAAAAGATACATATATAA
                                        2800
          *                   *                   *                   *                   *                   *
Val Leu Pro Gln Gly Trp Lys Gly Ser Pro Ala Ile Phe Gln His Thr Met Arg Gln Val
AGTCTTGCCACAGGGATGGAAGGGATCACCAGCAATTTTTCAACACACAATGAGACAGGT
          *                   *                   *                   *                   *                   *
Leu Glu Pro Phe Arg Lys Ala Asn Lys Asp Val Ile Ile Ile Gln Tyr Met Asp Asp Ile
ATTAGAACCATTCAGAAAAGCAAACAAGGATGTCATTATCATTCAGTACATGGATGATAT
                        2900
          *                   *                   *                   *                   *
Leu Ile Ala Ser Asp Arg Thr Asp Leu Glu His Asp Arg Val Val Leu Gln Leu Lys Glu
CTTAATAGCTAGTGACAGGACAGATTTAGAACATGATAGGGTAGTCCTGCAGCTCAAGGA
                                                                                                  3000
          *                   *                   *                   *                   *
Leu Leu Asn Gly Leu Gly Phe Ser Thr Pro Asp Glu Lys Phe Gln Lys Asp Pro Pro Tyr
ACTTCTAAATGGCCTAGGATTTTCTACCCCAGATGAGAAGTTCCAAAAAGACCCTCCATA
          *                   *                   *                   *                   *                   *
His Trp Met Gly Tyr Glu Leu Trp Pro Thr Lys Trp Lys Leu Gln Lys Ile Gln Leu Pro
CCACTGGATGGGCTATGAACTATGGCCAACTAAATGGAAGTTGCAGAAAATACAGTTGCC
                                        3100
          *                   *                   *                   *                   *                   *
Gln Lys Glu Ile Trp Thr Val Asn Asp Ile Gln Lys Leu Val Gly Val Leu Asn Trp Ala
CCAAAAAGAAATATGGACAGTCAATGACATCCAGAAGCTAGTGGGTGTCCTAAATTGGGC
          *                   *                   *                   *                   *                   *
Ala Gln Leu Tyr Pro Gly Ile Lys Thr Lys His Leu Cys Arg Leu Ile Arg Gly Lys Met
AGCACAACTCTACCCAGGGATAAAGACCAAACACTTATGTAGGTTAATCAGAGGAAAAAT
                              3200
          *                   *                   *                   *                   *
Thr Leu Thr Glu Glu Val Gln Trp Thr Glu Leu Ala Glu Ala Glu Leu Glu Glu Asn Arg
GACACTCAGAGAAGAAGTACAGTGGACAGAATTACCAGAAGCAGAGCTAGAAGAAAACAG
                                                                                                  3300
```

-continued

```
 Ile  Ile  Leu Ser  Gln Glu  Gln Glu  Gly  His  Tyr  Tyr  Gln Glu  Glu  Lys  Glu Leu Glu  Ala
AATTATCCTAAGCCAGGAACAAGAGGGACACTATTACCAAGAAGAAAAAGAGCTAGAAGC
 Thr Val  Gln Lys  Asp Gln  Glu Asn  Gln Trp  Thr Tyr  Lys  Ile  His  Gln Glu  Glu  Lys  Ile
AACAGTCCAAAAGGATCAAGAGAATCAGTGGACATATAAAATACACCAGGAAGAAAAAAT
                                                3400
 Leu Lys  Val  Gly Lys  Tyr  Ala Lys  Val  Lys  Asn Thr  His  Thr Asn Gly  Ile   Arg Leu  Leu
TCTAAAAGTAGGAAAATATGCAAAGGTGAAAAACACCCATACCAATGGAATCAGATTGTT
 Ala  Gln Val  Val  Gln Lys  Ile   Gly Lys  Glu  Ala Leu Val  Ile   Trp Gly  Arg  Ile  Pro  Lys
AGCACAGGTAGTTCAGAAAATAGGAAAAGAAGCACTAGTCATTTGGGGACGAATACCAAA
                         3500
 Phe His  Leu Pro  Val  Glu  Arg Glu  Ile   Trp Glu  Gln Trp  Trp Asp Asn Tyr  Trp Gln Val
ATTTCACCTACCAGTAGAGAGAGAAATCTGGGAGCAGTGGTGGGATAACTACTGGCAAGT
                                                                                     3600
 Thr Trp Ile   Pro Asp Trp  Asp Phe  Val Ser  Thr Pro  Pro Leu  Val  Arg Leu  Ala Phe  Asn
GACATGGATCCCAGACTGGGACTTCGTGTCTACCCCACCACTGGTCAGGTTAGCGTTTAA
 Leu Val  Gly  Asp Pro  Ile  Pro Gly  Ala Glu  Thr Phe  Tyr  Thr Asp Gly  Ser  Cys Asn  Arg
CCTGGTAGGGGATCCTATACCAGGTGCAGAGACCTTCTACACAGATGGATCCTGCAATAG
                                                3700
 Gln Ser  Lys  Glu  Gly  Lys  Ala  Gly  Tyr  Val  Thr Asp Arg  Gly  Lys  Asp Lys  Val  Lys  Lys
GCAATCAAAAGAAGGAAAAGCAGGATATGTAACAGATAGAGGGAAAGACAAGGTAAAGAA
 Leu Glu  Gln Thr  Thr Asn Gln Gln Ala  Glu Leu  Glu  Ala  Phe Ala  Met Ala  Leu Thr Asp
ACTAGAGCAAACTACCAATCAGCAAGCAGAACTAGAAGCCTTTGCGATGGCACTAACAGA
                            3800
 Ser Gly Pro  Lys  Val  Asn Ile  Ile   Val  Asp Ser  Gln Tyr  Val  Met Gly  Ile   Ser  Ala Ser
CTCGGGTCCAAAAGTTAATATTATAGTAGACTCACAGTATGTAATGGGGATCAGTGCAAG
                                                                                     3900
 Gln Pro Thr  Glu Ser  Glu Ser  Lys  Ile   Val  Asn Gln Ile   Ile   Glu Glu  Met Ile   Lys  Lys
CCAACCAACAGAGTCAGAAAGTAAAATAGTGAACCAGATCATAGAAGAAATGATAAAAAA
 Glu  Ala Ile   Tyr  Val  Ala  Trp Val  Pro Ala  His  Lys  Gly  Ile   Gly  Gly  Asn Gln Glu  Val
GGAAGCAATCTATGTTGCATGGGTCCCAGCCCACAAAGGCATAGGGGGAAACCAGGAAGT
                                                    4000
 Asp His  Leu Val  Ser  Gln Gly  Ile   Arg Gln Val  Leu  Phe  Leu Glu  Lys  Ile   Glu Pro  Ala
AGATCATTTAGTGAGTCAGGGTATCAGACAAGTGTTGTTCCTGGAAAAAATAGAGCCCGC
 Gln Glu  Glu  His  Glu Lys  Tyr  His  Ser  Asn Val  Lys  Glu Leu Ser  His  Lys  Phe  Gly  Ile
TCAGGAAGAACATGAAAAATATCATAGCAATGTAAAAGAACTGTCTCATAAATTTGGAAT
                         4100
 Pro Asn Leu  Val  Ala  Arg Gln Ile   Val  Asn Ser  Cys Ala  Gln Cys  Gln Gln Lys  Gly  Glu
ACCCAATTTAGTGGCAAGGCAAATAGTAAACTCATGTGCCCAATGTCAACAGAAGGGGA
                                                                                     4200
 Ala  Ile  His  Gly  Gln Val  Asn Ala  Glu Leu Gly  Thr Trp Gln Met Asp Cys  Thr His  Leu
AGCTATACATGGGCAAGTAAATGCAGAACTAGGCACTTGGCAAATGGACTGCACACATTT
 Glu  Gly  Lys  Ile   Ile   Ile   Val  Ala  Val  His  Val  Ala Ser  Gly  Phe  Ile   Glu  Ala  Glu  Val
AGAAGGAAAGATCATTATAGTAGCAGTACATGTTGCAAGTGGATTTATAGAAGCAGAAGT
                                                     4300
 Ile  Pro  Gln Glu  Ser  Gly  Arg Gln Thr  Ala Leu Phe  Leu Leu Lys  Leu  Ala Ser  Arg Trp
CATCCCACAGGAATCAGGAAGACAAACAGCACTCTTCCTATTGAAACTGGCAAGTAGGTG
 Pro  Ile  Thr  His  Leu His  Thr Asp Asn Gly  Ala  Asn Phe  Thr Ser  Gln Glu  Val  Lys  Met
GCCAATAACACACTTGCATACAGATAATGGTGCCAACTTCACTTCACAGGAGGTGAAGAT
                            4400
 Val  Ala  Trp Trp  Ile   Gly  Ile   Glu Gln Ser  Phe  Gly  Val  Pro  Tyr  Asn Pro  Gln Ser  Gln
GGTAGCATGGTGGATAGGTATAGAACAATCCTTTGGAGTACCTTACAATCCACAGAGCCA
                                                                                     4500
 Gly  Val  Val  Glu  Ala  Met Asn His  His  Leu Lys  Asn Glu  Ile   Ser  Arg  Ile   Arg Glu  Glu
AGGAGTAGTAGAAGCAATGAATCACCATCTAAAAAACCAAATAAGTAGAATCAGAGAACA
 Ala  Asn Thr  Ile   Glu Thr  Ile   Val  Leu Met Ala  Ile   His  Cys  Met Asn Phe  Lys  Arg  Arg
GGCAAATACAATAGAAACAATAGTACTAATGGCAATTCATTCCATGAATTTTAAAAGAAG
                                                    4600
 Gly  Gly  Ile   Gly  Asp Met Thr  Pro  Ser  Glu  Arg Leu  Ile   Asn Met Ile   Thr  Thr Glu  Gln
GGGGGGAATAGGGGATATGACTCCATCAGAAAGATTAATCAATATGATCACCACAGAACA
 Glu  Ile   Gln Phe  Leu Gln Ala  Lys  Asn Ser  Lys  Leu Lys  Asp Phe  Arg Val  Tyr  Phe  Arg
AGAGATACAATTCCTCCAAGCCAAAAATTCAAAATTAAAAGATTTTCGGGTCTATTTCAG
                         4700
 Glu  Gly  Arg  Asp Gln Leu Trp Lys  Gly  Pro  Gly  Gly  Leu Leu  Trp Lys  Gly  Glu  Gly  Ala
AGAAGGCAGAGATCAGTTGTGGAAAGGACCTGGGGAACTACTGTGGAAAGGAGAAGGAGC
                                                                                     4800
 Val  Leu Val  Lys  Val  Gly  Thr Asp Ile   Lys  Ile   Ile   Pro  Arg Arg Lys  Ala  Lys  Ile   Ile
AGTCCTAGTCAAGGTAGGAACAGACATAAAAATAATACCAAGAAGGAAAGCCAAGATCAT
```

-continued

```
Arg Asp Tyr Gly Gly Arg Gln Glu Met Asp Ser Gly Ser His Leu Glu Gly Ala Arg Glu
            Met Glu Glu Asp Lys Trp Trp Ile Val Val Pro Thr Trp Arg Val Pro Gly Arg
CAGAGACTATGGAGGAAGACAAGAGATGGATAGTGGTTCCCACCTGGAGGGTGCCAGGGA
                                                4900
Asp Gly Glu Met Ala
  Met Glu Lys Trp His Ser Leu Val Lys Tyr Leu Lys Tyr Lys Thr Lys Asp Leu Glu Lys
GGATGGAGAAATGGCATAGCCTTGTCAAGTATCTAAAATACAAAACAAAGGATCTAGAAA
 Val Cys Tyr Val Pro His His Lys Val Gly Trp Ala Trp Trp Thr Cys Ser Arg Val Ile
AGGTGTGCTATGTTCCCCACCATAAGGTGGGATGGGCATGGTGGACTTGCAGCAGGGTAA
                         5000
 Phe Pro Leu Lys Gly Asn Ser His Leu Glu Ile  Gln Ala Tyr Trp Asn Leu Thr Pro Glu
TATTCCCATTAAAAGGAAACAGTCATCTAGAGATACAGGCATATTGGAACTTAACACCAG
                                                               5100
    Lys Gly Trp Leu Ser Ser Tyr Ser Val Arg Ile  Thr Trp Tyr Thr Glu Lys Phe Trp Thr
AAAAAGGATGGCTCTCCTCTTATTCAGTAAGAATAACTTGGTACACAGAAAAGTTCTGGA
    Asp Val Thr Pro Asp Cys Ala Asp Val Leu Ile His Ser Thr Tyr Phe Pro Cys Phe Thr
CAGATGTTACCCCAGACTGTGCAGATGTCCTAATACATAGCACTTATTTCCCTTGCTTTA
                                  5200
    Ala Gly Glu Val Arg Arg Ala Ile  Arg Gly Glu Lys Leu Leu Ser Cys Cys Asn Tyr Pro
CAGCAGGTGAAGTAAGAAGAGCCATCAGAGGGGAAAAGTTATTGTCCTGCTGCAATTATC
     Arg Ala His Arg Ala Gln Val Pro Ser Leu Gln Phe Leu Ala Leu Val Val Val Gln Gln
CCCGAGCTCATAGAGCCCAGGTACCGTCACTTCAATTTCTGGCCTTAGTGGTAGTGCAAC
                          5300
      Met Thr Asp Pro Arg Glu Thr Val Pro Pro Gly Asn Ser Gly Glu Glu Thr Ile  Gly
    Asn Asp Arg Pro Gln Arg Asp Ser Thr Thr Arg Lys Gln Arg Arg Arg Asp Tyr Arg Arg
AAAATGACAGACCCCAGAGAGACAGTACCACCAGGAAACAGCGGCGAAGAGACTATCGGA
                                                           5400
Glu Ala Phe Ala Trp Leu Asn Arg Thr Val Glu Ala Ile  Asn Arg Glu Ala Val Asn His
  Gly Leu Arg Ala Leu Ala Lys Gln Asp Ser Arg Ser His Lys Gln Arg Ser Ser Glu Ser Pro
GAGGCCTTCGCCTGGCTAAACAGGACAGTAGAAGCCATAAACAGAGAAGCAGTGAATCAC
Leu Pro Arg Glu Leu Ile  Phe Gln Val Trp Gln Arg Ser Trp Arg Tyr Trp His Asp Glu
    Thr Pro Arg Thr Tyr Phe Pro Gly Val Ala Glu Val Leu Glu Ile  Leu Ala
CTACCCCGAGAACTTATTTTCCAGGTGTGGCAGAGGTCCTGGAGATACTGGCATGATGAA
                                    5500
Gln Gly Met Ser Glu Ser Tyr Thr Lys Tyr Arg Tyr Leu Cys Ile  Ile  Gln Lys Ala Val
CAAGGGATGTCAGAAAGTTACACAAAGTATAGATATTTGTGCATAATACAGAAAGCAGTG
Tyr Met His Val Arg Lys Gly Cys Thr Cys Leu Gly Arg Gly His Gly Pro Gly Gly Trp
TACATGCATGTTAGGAAAGGGTGTACTTGCCTGGGGAGGGGACATGGGCCAGGAGGGTGG
                       5600
Arg Pro Gly Pro Pro Pro Pro Pro Pro Gly Leu Val
                                   Met Ala Glu Ala Pro Thr Glu
AGACCAGGGCCTCCTCCTCCTCCCCCTCCAGGTCTGGTCTAATGGCTGAAGCACCAACAG
                                                          5700
    Leu Pro Pro Val Asp Gly Thr Pro Leu Arg Glu Pro Gly Asp Glr Trp Ile  Ile  Glu Ile
AGCTCCCCCCGGTGGATGGGACCCCACTGAGGGAGCCAGGGGATGAGTGGATAATAGAAA
    Leu Arg Glu Ile  Lys Glu Glu Ala Leu Lys His Phe Asp Pro Arg Leu Leu Ile  Ala Leu
TCTTGAGAGAAATAAAAGAAGAAGCTTTAAAGCATTTTGACCCTCGCTTGCTAATTGCTC
                                 5800
                      Met Glu Thr Pro Leu Lys Ala Pro Glu Ser Ser Leu
   Gly Lys Tyr Ile  Tyr Thr Arg His Gly Asp Thr Leu Glu Gly Ala Arg Glu Leu Ile  Lys
TTGGCAAATATATCTATACTAGACATGGAGACACCCTTGAAGGCGCCAGAGAGCTCATTA
Lys Ser Cys Asn Glu Pro Phe Ser Arg Thr Ser Glu Gln Asp Val Ala Thr Gln Glu Leu
   Val Leu Gln Arg Ala Leu Phe Thr His Phe Arg Ala Gly Cys Gly His Ser Arg Ile  Gly
AAGTCCTGCAACGAGCCCTTTTCACGCACTTCAGAGCAGGATGTGGCCACTCAAGAATTG
                          5900
Ala Arg Gln Gly Glu Glu Ile  Leu Ser Gln Leu Tyr Arg Pro Leu Glu Thr Cys Asn Asn
   Gln Thr Arg Gly Gly Asn Pro Leu Ser Ala Ile  Pro Thr Pro Arg Asn Met Gln
GCCAGACAAGGGGAGGAAATCCTCTCTCAGCTATACCGACCCCTAGAAACATGCAATAAC
                                                        6000
Ser Cys Tyr Cys Lys Arg Cys Cys Tyr His Cys Gln Met Cys Phe Leu Asn Lys Gly Leu
TCATGCTATTGTAAGCGATGCTGCTACCATTGTCAGATGTGTTTTCTAAACAAGGGGCTC
Gly Ile  Cys Tyr Glu Arg Lys Gly Arg Arg Arg Arg Thr Pro Lys Lys Thr Lys Thr His
          Met Asn Glu Arg Ala Asp Glu Glu Gly Leu Gln Arg Lys Leu Arg Leu Ile
GGGATATGTTATGAACGAAAGGGCAGACGAAGAAGGACTCCAAAGAAAACTAAGACTCAT
                                 6100
Pro Ser Pro Thr Pro Asp Lys
  Arg Leu Leu His Gln Thr
                         Met Met Asn Gln Leu Leu Ile  Ala Ile  Leu Leu Ala
CCGTCTCCTACACCAGACAAGTGAGTATGATGAATCAGCTGCTTATTGCCATTTTATTAG
```

-continued

```
Ser Ala Cys Leu Val Tyr Cys Thr Gln Tyr Val Thr Val Phe Tyr Gly Val Pro Thr Trp
CTAGTGCTTGCTTAGTATATTGCACCCAATATGTAACTGTTTTCTATGGCGTACCCACGT
                                6200
Lys Asn Ala Thr Ile Pro Leu Phe Cys Ala Thr Arg Asn Arg Asp Thr Trp Gly Thr Ile
GGAAAAATGCAACCATTCCCCTCTTTTGTGCAACCAGAAATAGGGATACTTGGGGAACCA
                                                                6300
Gln Cys Leu Pro Asp Asn Asp Asp Tyr Gln Glu Ile Thr Leu Asn Val Thr Glu Ala Phe
TACAGTGCTTGCCTGACAATGATGATTATCAGGAAATAACTTTGAATGTAACAGAGGCTT
Asp Ala Trp Asn Asn Thr Val Thr Glu Gln Ala Ile Glu Asp Val Trp His Leu Phe Glu
TTGATGCATGGAATAATACAGTAACAGAACAAGCAATAGAAGATGTCTGGCATCTATTCG
                                6400
Thr Ser Ile Lys Pro Cys Val Lys Leu Thr Pro Leu Cys Val Ala Met Lys Cys Ser Ser
AGACATCAATAAAACCATGTGTCAAACTAACACCTTTATGTGTAGCAATGAAATGCAGCA
Thr Glu Ser Ser Thr Gly Asn Asn Thr Thr Ser Lys Ser Thr Ser Thr Thr Thr Thr Thr
GCACAGAGAGCAGCACAGGGAACAACACAACCTCAAAGAGCACAAGCACAACCACAACCA
                                6500
Pro Thr Asp Gln Glu Gln Glu Ile Ser Glu Asp Thr Pro Cys Ala Arg Ala Asp Asn Cys
CACCCACAGACCAGGAGCAAGAGATAAGTGAGGATACTCCATGCGCACGCGCAGACAACT
                                                                6600
Ser Gly Leu Gly Glu Glu Glu Thr Ile Asn Cys Gln Phe Asn Met Thr Gly Leu Glu Arg
GCTCAGGATTGGGAGAGGAAGAAACGATCAATTGCCAGTTCAATATGACAGGATTAGAAA
Asp Lys Lys Lys Gln Tyr Asn Glu Thr Trp Tyr Ser Lys Asp Val Val Cys Glu Thr Asn
GAGATAAGAAAAAACAGTATAATGAAACATGGTACTCAAAAGATGTGGTTTGTGAGACAA
                                6700
Asn Ser Thr Asn Gln Thr Gln Cys Tyr Met Asn His Cys Asn Thr Ser Val Ile Thr Glu
ATAATAGCACAAATCAGACCCAGTGTTACATGAACCATTGCAACACATCAGTCATCACAG
Ser Cys Asp Lys His Tyr Trp Asp Ala Ile Arg Phe Arg Tyr Cys Ala Pro Pro Gly Tyr
AATCATGTGACAAGCACTATTGGGATGCTATAAGGTTTAGATACTGTGCACCACCGGGTT
                                6800
Ala Leu Leu Arg Cys Asn Asp Thr Asn Tyr Ser Gly Phe Ala Pro Asn Cys Ser Lys Val
ATGCCCTATTAAGATGTAATGATACCAATTATTCAGGCTTTGCACCCAACTGTTCTAAAG
                                                                6900
Val Ala Ser Thr Cys Thr Arg Met Met Glu Thr Gln Thr Ser Thr Trp Phe Gly Phe Asn
TAGTAGCTTCTACATGCACCAGGATGATGGAAACGCAAACTTCCACATGGTTTGGCTTTA
Gly Thr Arg Ala Glu Asn Arg Thr Tyr Ile Tyr Trp His Gly Arg Asp Asn Arg Thr Ile
ATGGCACTAGAGCAGAGAATAGAACATATATCTATTGGCATGGCAGAGATAATAGAACTA
                                7000
Ile Ser Leu Asn Lys Tyr Tyr Asn Leu Ser Leu His Cys Lys Arg Pro Gly Asn Lys Thr
TCATCAGCTTAAACAAATATTATAATCTCAGTTTGCATTGTAAGAGGCCAGGGAATAAGA
Val Lys Gln Ile Met Leu Met Ser GlyHis Val Phe His Ser His Tyr Gln Pro Ile Asn
CAGTGAAACAAATAATGCTTATGTCAGACATGTGTTTCACTCCCACTACCAGCCGATCA
                                7100
Lys Arg Pro Arg Gln Ala Trp Cys Trp Phe Lys Gly Lys Trp Lys Asp Ala Met Gln Glu
ATAAAAGACCCAGACAAGCATGGTGCTGGTTCAAAGGCAAATGGAAAGACGCCATGCAGG
                                                                7200
Val Lys Glu Thr Leu Ala Lys His Pro Arg Tyr Arg Gly Thr Asn Asp Thr Arg Asn Ile
AGGTGAAGGAAACCCTTGCAAAACATCCCAGGTATAGAGGAACCAATGACACAAGGAATA
Ser Phe Ala Ala Pro Gly Lys Gly Ser Asp Pro Glu Val Ala Tyr Met Trp Thr Asn Cys
TTAGCTTTGCAGCGCCAGGAAAAGGCTCAGACCCAGAAGTAGCATACATGTGGACTAACT
                                7300
Arg Gly Glu Phe Leu Tyr Cys Asn Met Thr Trp Phe Leu Asn Trp Ile Glu Asn Lys Thr
GCAGAGGAGAGTTTCTCTACTGCAACATGACTTGGTTCCTCAATTGGATAGAGAATAAGA
His Arg Asn Tyr Ala Pro Cys His Ile Lys Gln Ile Ile Asn Thr Trp His Lys Val Gly
CACAGCGCAATTATGCACCGTGCCATATAAAGCAAATAATTAACACATGGCATAAGGTAG
                                7400
Arg Asn Val Tyr Leu Pro Pro Arg Glu Gly Glu Leu Ser Cys Asn Ser Thr Val Val Ser
GGAGAAATGTATATTTGCCTCCCAGGGAAGGGGAGCTGTCCTGCAACTCAACAGTAACCA
                                                                7500
Ile Ile Ala Asn Ile Asp Trp Gln Asn Asn Asn Gln Thr Asn Ile Thr Phe Ser Ala Glu
GCATAATTGCTAACATTGACTGGCAAAACAATAATCAGACAAACATTACCTTTAGTGCAG
Val Ala Glu Leu Tyr Arg Leu Glu Leu Gly Asp Tyr Lys Leu Val Glu Ile Thr Pro Ile
AGGTGGCAGAACTATACAGATTGGAGTTGGGAGATTATAAATTGGTAGAAATAACACCAA
                                7600
Gly Phe Ala Pro Thr Lys Glu Lys Arg Tyr Ser Ser Ala His Gly Arg His Thr Arg Gly
TTGGCTTCGCACCTACAAAAGAAAAAAGATACTCCTCTGCTCACGGGAGACATACAAGAG
```

-continued

```
        Val  Phe  Val  Leu  Gly  Phe  Leu  Gly  Phe  Leu  Ala  Thr  Ala  Gly  Ser  Ala  Met  Gly  Ala  Ala
        GTGTGTTCGTGCTAGGGTTCTTGGGTTTTCTCGCAACAGCAGGTTCTGCAATGGGCGCGG
                                        7700
        Ser  Leu  Thr  Val  Ser  Ala  Gln  Ser  Arg  Thr  Leu  Leu  Ala  Gly  Ile  Val  Gln  Gln  Gln  Gln
        CGTCCCTGACCGTGTCGGCTCAGTCCCGGACTTTACTGGCCGGGATAGTGCAGCAACAGC
                                                                                                   7800
        Gln  Leu  Leu  Asp  Val  Val  Lys  Arg  Gln  Gln  Glu  Leu  Leu  Arg  Leu  Thr  Val  Trp  Gly  Thr
        AACAGCTGTTGCACGTGGTCAAGAGACAACAAGAACTGTTGCGACTGACCGTCTGGGGAA
        Lys  Asn  Leu  Gln  Ala  Arg  Val  Thr  Ala  Ile  Glu  Lys  Tyr  Leu  Gln  Asp  Gln  Ala  Arg  Leu
        CGAAAAACCTCCAGGCAACAGTCACTGCTATAGAGAAGTACCTACAGGACCAGGCGCGGC
                                        7900
        Asn  Ser  Trp  Gly  Cys  Ala  Phe  Arg  Gln  Val  Cys  His  Thr  Thr  Val  Pro  Trp  Val  Asn  Asp
        TAAATTCATGGGGATGTGCGTTTAGACAAGTCTGCCACACTACTGTACCATGGGTTAATG
        Ser  Leu  Ala  Pro  Asp  Trp  Asp  Asn  Met  Thr  Trp  Gln  Glu  Trp  Glu  Lys  Gln  Val  Arg  Tyr
        ATTCCTTAGCACCTGACTGGGACAATATGACGTGGCAGGAATGGGAAAAACAAGTCCGCT
                                        8000
        Leu  Glu  Ala  Asn  Ile  Ser  Lys  Ser  Leu  Glu  Gln  Ala  Gln  Ile  Gln  Gln  Glu  Lys  Asn  Met
        ACCTGGAGGCAAATATCAGTAAAAGTTTAGAACAGGCACAAATTCAGCAAGAGAAAAATA
                                                                                                   8100
        Tyr  Glu  Leu  Gln  Lys  Leu  Asn  Ser  Trp  Asp  Ile  Phe  Gly  Asn  Trp  Phe  Asp  Leu  Thr  Ser
        TGTATGAACTACAAAAATTAAATAGCTGGGATATTTTTGGCAATTGGTTTGACTTAACCT
        Trp  Val  Lys  Tyr  Ile  Gln  Tyr  Gly  Val  Leu  Ile  Ile  Val  Ala  Val  Ile  Ala  Leu  Arg  Ile
        CCTGGGTCAAGTATATTCAATATGGAGTGCTTATAATAGTAGCAGTAATAGCTTTAAGAA
                                        8200
        Val  Ile  Tyr  Val  Val  Gln  Met  Leu  Ser  Arg  Leu  Arg  Lys  Gly  Tyr  Arg  Pro  Val  Phe  Ser
        TAGTGATATATGTAGTACAAATGTTAAGTAGGCTTAGAAAGGGCTATAGGCCTGTTTTCT
                                                     Ser  Ile  Ser  Thr  Arg  Thr  Gly  Asp  Ser  Gln  Pro
                                                Asn  Pro  Tyr  Pro  Gln  Gly  Pro  Gly  Thr  Ala  Ser  Gln
        Ser  Pro  Pro  Gly  Tyr  Ile  Gln  Gln  Ile  His  Ile  His  Lys  Asp  Arg  Gly  Gln  Pro  Ala  Asn
        CTTCCCCCCCCGGTTATATCCAACAGATCCATATCCACAAGGACCGGGGACAGCCAGCCA
                        8300
        Thr  Lys  Lys  Gln  Lys  Lys  Thr  Val  Glu  Ala  Thr  Val  Glu  Thr  Asp  Thr  Gly  Pro  Gly  Arg
          Arg  Arg  Asn  Arg  Arg  Arg  Arg  Trp  Lys  Gln  Arg  Trp  Arg  Gln  Ile  Leu  Ala  Leu  Ala  Asp
           Glu  Glu  Thr  Glu  Glu  Asp  Gly  Gly  Ser  Asn  Gly  Gly  Asp  Arg  Tyr  Trp  Pro  Trp  Pro  Ile
        ACGAAGAAACAGAAGAAGACGGTGGAAGCAACGGTGGAGACAGATACTGGCCCTGGCCGA
                                                                                                   8400
        Ser  Ile  Tyr  Thr  Phe  Pro  Asp  Pro  Pro  Ala  Asp  Ser  Pro  Leu  Asp  Gln  Thr  Ile  Gln  His
          Ala  Tyr  Ile  His  Phe  Leu  Ile  Arg  Gln  Leu  Ile  Arg  Leu  Leu  Thr  Arg  Leu  Tyr  Ser  Ile
        TAGCATATATACATTTCCTGATCCGCCAGCTGATTCGCCTCTTGACCAGACTATACAGCA
        Leu  Gln  Gly  Leu  Thr  Ile  Gln  Glu  Leu  Pro  Asp  Pro  Pro  Thr  His  Leu  Pro  Glu  Ser  Gln
          Cys  Arg  Asp  Leu  Leu  Ser  Arg  Ser  Phe  Leu  Thr  Leu  Gln  Leu  Ile  Tyr  Gln  Asn  Leu  Arg
        TCTGCAGGGACTTACTATCCAGGAGCTTCCTGACCCTCCAACTCATCTACCAGAATCTCA
                                                     8500
        Arg  Leu  AlA  Glu  Thr                                  Met  Gly  Ala  Ser  Gly  Ser  Lys  Lys
           Asp  Trp  Leu  Arg  Leu  Arg  Thr  Ala  Phe  Leu  Ala  Ile  Tyr  Gly  Cys  Glu  Trp  Ile  Gln  Glu  Ala
        GAGACTGGCTGAGACTTAGAACAGCCTTCTTGCAATATGGGTGCGAGTGGATCCAAGAAG
        His  Ser  Arg  Pro  Pro  Arg  Gly  Leu  Gln  Glu  Arg  Leu  Leu  Arg  Ala  Arg  Ala  Gly  Ala  Cys
           Phe  Gln  Ala  Ala  Ala  Arg  Ala  Thr  Arg  Glu  Thr  Leu  Ala  Gly  Ala  Cys  Arg  Gly  Leu  Trp
        CATTCCAGGCCGCCGCGAGGGCTACAAGAGAGACTCTTGCGGGCGCGTGCAGGGGCTTGT
                                8600
        Gly  Gly  Tyr  Trp  Asn  Glu  Ser  Gly  Gly  Glu  Tyr  Ser  Arg  Phe  Gln  Glu  Gly  Ser  Asp  Arg
           Arg  Val  Leu  Glu  Arg  Ile  Gly  Arg  Gly  Ile  Leu  Ala  Val  Pro  Arg  Arg  Ile  Arg  Gln  Gly
        GCAGGGTATTGGAACGAATCGGGAGGGGAATACTCGCGGTTCCAAGAAGGATCAGACAGG
                                                                                                   8700
        Glu  Gln  Lys  Ser  Pro  Ser  Cys  Glu  Gly  Arg  Gln  Tyr  Gln  Gln  Gly  Asp  Phe  Met  Asn  Thr
          Ala  Glu  Ile  Ala  Leu  Leu
        GAGCAGAAATCGCCCTCCTGTGAGGGACGGCAGTATCAGCAGGGAGACTTTATGAATACT
        Pro  Trp  Lys  Asp  Pro  Ala  Ala  Glu  Arg  Glu  Lys  Asn  Leu  Tyr  Arg  Gln  Gln  Asn  Met  Asp
        CCATGGAAGGACCCAGCAGCAGAAAGGGAGAAAAATTTGTACAGGCAACAAAATATGGAT
                                                                        8800
        Asp  Val  Asp  Ser  Asp  Asp  Asp  Gln  Val  Arg  Val  Ser  Val  Thr  Pro  Lys  Val  Pro  Leu
        GATGTAGATTCAGATGATGATGACCAAGTAAGAGTTTCTGTCACACCAAAAGTACCACTA
        Arg  Pro  Met  Thr  His  Arg  Leu  Ala  Ile  Asp  Met  Ser  His  Leu  Ile  Lys  Thr  Arg  Gly  Gly
        AGACCAATGACACATAGATTGGCAATAGATATGTCACATTTAATAAAAACAAGGGGGGGA
                                        8900
        Leu  Glu  Gly  Met  Phe  Tyr  Ser  Glu  Arg  Arg  His  Lys  Ile  Leu  Asn  Ile  Tyr  Leu  Leu  Lys
        CTGGAAGGGATGTTTTACAGTGAAAGAAGACATAAAATCTTAAATATATACTTAGAAAAG
                                                                                                   9000
```

-continued

```
                *               *                *              *                *
Glu Glu Gly Ile Ile Ala Asp Trp Gln Asn Tyr Thr His Gly Pro Gly Val Arg Tyr Pro
CAAGAAGGGATAATTGCAGATTGGCAGAACTACACTCATGGGCCAGGAGTAAGATACCCA
                *               *                *              *                *
Met Phe Phe Gly Trp Leu Trp Lys Leu Val Pro Val Asp Val Pro Gln Glu Gly Glu Asp
ATGTTCTTTGGGTGGCTATGGAAGCTAGTACCAGTAGATGTCCCACAAGAAGGGGAGCAC
                                         9100
                *               *                *              *                *
Thr Glu Thr Thr Cys Leu Val His Pro Ala Gln Thr Ser Lys Phe Asp Asp Pro His Gly
ACTGAGACTCACTGCTTAGTACATCCAGCACAAACAAGCAAGTTTGATGACCCGCATGGG
                *               *                *              *                *
Glu Thr Leu Val Trp Glu Phe Asp Pro Leu Leu Ala Tyr Ser Tyr Glu Ala Phe Ile Arg
GAGACACTAGTCTGGGAGTTTGATCCCTTGCTGGCTTATAGTTACGAGGCTTTTATTCGG
                      9200
                *               *                *              *                *
Tyr Pro Glu Glu Phe Gly His Lys Ser Gly Leu Pro Glu Glu Glu Trp Lys Ala Arg Leu
TACCCAGAGGAATTTGGGCACAAGTCAGGCCTGCCAGAGGAAGAGTGGAAGGCGAGACTG
                                                                       9300
                *               *                *              *                *
Lys Ala Arg Gly Ile Pro Phe Ser
AAAGCAAGAGGAATACCATTTAGTTAAAGACAGGAACAGCTATACTTGGTCAGGGCAGGA
                *               *                *              *                *
AGTAACTAACAGAAACAGCTGAGACTGCAGGGACTTTCCAGAAGGGGCTGTAACCAAGGG
                                         9400
                *               *                *              *                *
AGGGACATGGGAGGAGCTGGTGGGGAACGCCCTCATATTCTCTGTATAAATATACCCGCT
                *               *                *              *                *
AGCTTGCATTGTACTTCGGTCGCTCTGCGGAGAGGCTGGCAGATTGAGCCCTGGGAGGTT
                      9500
                *               *                *              *                *
CTCTCCAGCAGTAGCAGGTAGAGCCTGGGTGTTCCCTGCTAGACTCTCACCAGCACTTGG
                                                                       9600
                *               *                *              *                *
CCGGTGCTGGGCAGACGGCCCCACGCTTGCTTGCTTAAAAACCTCCTTAATAAAGCTGCC
                *               *                *              *                *
AGTTAGAAGCA
                *
```

Example 5

Sequences of the Coding Regions for the Envelope Protein and GAG Product of the ROD HIV-2 Isolate Through experimental analysis of the HIV-2 ROD isolate, the following sequences were identified for the regions encoding the env and gag gene products. One of ordinary skill in the art will recognize that the numbering for both gene regions which follow begins for convenience with "1" rather than the corresponding number for its initial nucleotide as given in Example 4, above, in the context of the complete genomic sequence.

<u>Envelope sequence</u>

```
Met Met Asn Gln Leu Leu Ile Ala Ile Leu Leu Ala Ser Ala Cys
ATGATGAATCAGCTGCTTATTGCCATTTTATTAGCTAGTGCTTGC
             *           *           *           *

Leu Val Tyr Cys Thr Gln Tyr Val Thr Val Phe Tyr Gly Val Pro
TTAGTATATTGCACCCAATATGTAACTGTTTTCTATGGCGTACCC
      *           *           *           *           *

Thr Trp Lys Asn Ala Thr Ile Pro Leu Phe Cys Ala Thr Arg Asn
ACGTGGAAAAATGCAACCATTCCCCTGTTTTGTGCAACCAGAAAT
           100           *           *           *

Arg Asp Thr Trp Gly Thr Ile Gln Cys Leu Pro Asp Asn Asp Asp
AGGGATACTTGGGGAACCATACAGTGCTTGCCTGAGAATGATGAT
      *           *           *           *           *

Tyr Gln Glu Ile Thr Leu Asn Val Thr Glu Ala Phe Asp Ala Trp
TATCAGGAAATAACTTTGAATGTAACAGAGGCTTTTGATGCATGG
             *         200               *           *

Asn Asn Thr Val Thr Glu Gln Ala Ile Glu Asp Val Trp His Leu
AATAATACAGTAACAGAACAAGCAATAGAAGATGTCTGGCATCTA
      *           *           *           *           *

Phe Glu Thr Ser Ile Lys Pro Cys Val Lys Leu Thr Pro Leu Cys
TTCGAGACATCAATAAAACCATGTGTGAAACTAACACCTTTATGT
             *           *          300          *

Val Ala Met Lys Cys Ser Ser Thr Glu Ser Ser Thr Gly Asn Asn
GTAGCAATGAAATGCAGCAGCACAGAGAGCAGCACAGGGAACAAC
      *           *           *           *           *
```

```
Thr Thr Ser Lys Ser Thr Ser Thr Thr Thr Thr Thr Pro Thr Asp
ACAACCTCAAAGAGCACAAGCACAACGACAACCACACCCAGAGAC
          *              *              *            400

Gln Glu Gln Glu Ile  Ser Glu Asp Thr Pro Cys Ala Arg Ala Asp
CAGGAGCAAGAGATAAGTGAGGATACTCCATGCGCACGCGCAGAG
          *              *              *              *              *

Asn Cys Ser Gly Leu Gly Glu Glu Glu Thr Ile  Asn Cys Gln Phe
AACTGCTCAGGATTGGGAGAGGAAGAAACGATCAATTGCCAGTTC
          *              *              *              *

Asn Met Thr Gly Leu Glu Arg Asp Lys Lys Lys Gln Tyr Asn Glu
AATATGACAGGATTAGAAAGAGATAAGAAAAAACAGTATAATGAA
    500                  *              *              *              *

Thr Trp Tyr Ser Lys Asp Val Val Cys Glu Thr Asn Asn Ser Thr
ACATGGTAGTCAAAAGATGTGGTTTGTGAGACAAATAATAGCACA
          *              *              *              *

Asn Gln Thr Gln Cys Tyr Met Asn His Cys Asn Thr Ser Val Ile
AATCAGACCCAGTGTTACATGAACCATTGCAACACATCAGTCATC
          *           600               *              *              *

Thr Glu Ser Cys Asp Lys His Tyr Trp Asp Ala Ile  Arg Phe Arg
ACAGAATCATGTGACAAGCACTATTGGGATGCTATAAGGTTTAGA
          *              *              *              *              *

Tyr Cys Ala Pro Pro Gly Tyr Ala Leu Leu Arg Cys Asn Asp Thr
TACTGTGCACCACGGGGTTATGCCCTATTAAGATGTAATGATACC
          *              *           700               *              *

Asn Tyr Ser Gly Phe Ala Pro Asn Cys Ser Lys Val Val Ala Ser
AATTATTCAGGCTTTGCACCCAACTGTTCTAAAGTAGTAGCTTCT
          *              *              *              *

Thr Cys Thr Arg Met Met Glu Thr Gln Thr Ser Thr Trp Phe Gly
ACATGCACCAGGATGATGGAAACGCAAACTTCCACATGGTTTGGC
          *              *              *           800              *

Phe Asn Gly Thr Arg Ala Glu Asn Arg Thr Tyr Ile  Tyr Trp His
TTTAATGGCACTAGAGCAGAGAATAGAAGATATATCTATTGGCAT
          *              *              *              *

Gly Arg Asp Asn Arg Thr Ile  Ile  Ser Leu Asn Lys Tyr Tyr Asn
GGCAGAGATAATAGAACTATCATCAGCTTAAACAAATATTATAAT
          *              *              *              *           900

Leu Ser Leu His Cys Lys Arg Pro Gly Asn Lys Val Lys Gln
CTCAGTTTGCATTGTAAGAGGCCAGGGAATAAGGTGAAACAA
          *              *              *              *

Ile  Met Leu Met Ser Gly His Val Phe His Ser His Tyr Gln Pro
ATAATGCTTATGTCAGGACATGTGTTTCACTCCCACTACCAGCCG
          *              *              *              *              *

↓
Ple Asn Lys Arg Pro Arg Gln Ala Trp Cys Trp Phe Lys Gly Lys
ATCAATAAAAGACCCAGACAAGCATGGTGCTGGTTCAAAGGCAAA
       1000              *              *              *

↓
Trp Lys Asp Ala Met Gln Glu Val Lys Thr Leu Ala Lys His Pro
TGGAAAGACGCCATGGAGGAGGTGAAGAGCCTTGCAAAACATCCC
          *              *              *              *              *

Arg Tyr Arg Gly Thr Asn Asp Thr Arg Asn Ile  Ser Phe Ala Ala
AGGTATAGAGGAACCAATGACACAAGGAATATTAGGTTTGCAGCG
          *           1100              *              *

Pro Gly Lys Gly Ser Asp Pro Glu Val Ala Tyr Met Trp Thr Asn
CCAGGAAAAGGCTCAGACCCAGAAGTAGCATACATGTGGACTAAC
          *              *              *              *              *

Cys Arg Gly Glu Phe Leu Tyr Cys Asn Met Thr Trp Phe Leu Asn
TGCAGAGGAGAGTTTCTCTACTGCAACATGACTTGGTTCCTCAAT
          *              *           1200             *

Trp Ile  Glu Asn Lys Thr His Arg Asn Tyr Ala Pro Cys His Ile
TGGATAGAGAATAAGACACACCGCAATTATGCACCGTGCCATATA
          *              *              *              *
```

```
Lys Gln Ile  Ile  Asn Thr Trp His Lys Val Gly Arg Asn Val Tyr
AAGCAAATAATTAACACATGGCATAAGGTAGGGAGAAATGTATAT
         *             *             *       1300

Leu Pro Pro Arg Glu Gly Glu Leu Ser Asn Ser Thr Val Thr
TTGCCTCCCAGGGAAGGGGAGCTGTGCAACTCAACAGTAACC
       *         *         *         *         *

Ser Ile  Ile  Ala Asn Ile  Asp Trp Gln Asn Asn Asn Gln Thr Asn
AGCATAATTGCTAACATTGACTGGCAAAACAATAATCAGACAAAC
       *         *         *         *

Ile  Thr Phe Ser Ala Glu Val Ala Glu Leu Tyr Arg Leu Glu Leu
ATTACCTTTAGTGCAGAGGTGGCAGAACTATACAGATTGGAGTTG
  1400           *         *         *         *

Gly Asp Tyr Lys Leu Val Glu Ile  Thr Pro Ile  Gly Phe Ala Pro
GGAGATTATAAATTGGTAGAAATAACACCAATTGGCTTCGCACCT
         *         *         *         *

Thr Lys Glu Lys Arg Tyr Ser Ser Ala His Gly Arg His Thr Arg
ACAAAAGAAAAAAGATACTCCTCTGCTGACGGGAGACATACAAGA
       *       1500        *         *         *

Gly Val Phe Val Leu Gly Phe Leu Gly Phe Leu Ala Thr Ala Gly
GGTGTGTTCGTGCTAGGGTTCTTGGGTTTTCTCGCAACAGCAGGT
         *         *         *         *

Ser Ala Met Gly Ala Arg Ala Ser Leu Thr Val Ser Ala Gln Ser
TCTGCAATGGGCGCTCGAGCGTCCCTGACCGTGTCGGCTCAGTGC
       *         *       1600        *         *

Arg Thr Leu Leu Ala Gly Ile  Val Gln Gln Gln Gln Gln Leu Leu
CGGACTTTACTGGCCGGGATAGTGCAGCAACAGCAACAGCTGTTG
       *         *         *         *         *

Asp Val Val Lys Arg Gln Gln Glu Leu Leu Arg Leu Thr Val Trp
GACGTGGTCAAGAGACAACAAGAACTGTTGCGAGTGACCGTCTCG
       *         *         *       1700        *

Gly Thr Lys Asn Leu Gln Ala Arg Val Thr Ala Ile  Glu Lys Tyr
GGAACGAAAAACCTCCAGGCAAGAGTCACTGCTATAGAGAAGTAG
       *         *         *         *

Leu Glu Asp Gln Ala Arg Leu Asn Ser Trp Gly Cys Ala Phe Arg
CTACAGGACCAGGCGCGGCTAAATTCATGGGGATCTGCGTTTAGA
       *         *         *         *       1800

Gln Val Cys His Thr Thr Val Pro Trp Val Asn Asp Ser Leu Ala
CAAGTCTGCCACACTACTGTACCATGGGTTAATGATTCCTTAGGA
       *         *         *         *

Pro Asp Trp Asp Asn Met Thr Trp Gln Glu Trp Glu Lys Gln Val
CCTGACTGGGACAATATGACGTGGCAGGAATGGGAAAAACAAGTC
       *         *         *         *         *

Arg Tyr Leu Glu Ala Asn Ile  Ser Lys Ser Leu Glu Gln Ala Gln
CGCTACCTGGAGGCAAATATCAGTAAAAGTTTAGAACAGGCACAA
       1900        *         *         *

Ile  Gln Gln Glu Lys Asn Met Tyr Glu Leu Gln Lys Leu Asn Ser
ATTCAGCAAGAGAAAAATATGTATGAACTACAAAAATTAAATACC
       *         *         *         *         *

Trp Asp Ile  Phe Gly Asn Trp Phe Asp Leu Thr Ser Trp Val Lys
TGGGATATTTTTGGCAATTGGTTTGACTTAACCTCCTGGGTCAAG
         *       2000        *         *

Tyr Ile  Gln Tyr Gly Val Leu Ile  Ile  Val Ala Val Ile  Ala Leu
TATATTCAATATGGAGTGCTTATAATAGTAGCAGTAATAGCTTTA
       *         *         *         *         *

Arg Ile  Val Ile  Tyr Val Val Gln Met Leu Ser Arg Leu Arg Lys
AGAATAGTGATATATGTAGTACAAATGTTAAGTAGGCTTAGAAAG
         *         *       2100        *

Gly Tyr Arg Pro Val Phe Ser Ser Pro Pro Gly Tyr Ile  Gln ***
GGCTATAGGCCTGTTTTCTCTTCCCCCCCCGGTTATATCCAATAG

Ile  His Ile  His Lys Asp Arg Gly Gln Pro Ala Asn Glu Glu Thr
ATCCATATCCACAAGGACCGGGGACAGCCAGCCAACGAAGAAACA
         *         *         *       2200
```

-continued

```
Glu Glu Asp Gly Gly Ser Asn Gly Gly Asp Arg Tyr Trp Pro Trp
GAAGAAGACGGTGGAAGCAACGGTGGAGACAGATACTGGCCCTGG
    *         *         *         *         *

Pro Ile Ala Tyr Ile His Phe Leu Ile Arg Gln Leu Ile Arg Leu
GCGATAGCATATATACATTTCCTCATCCGCCAGCTGATTGGGCTC
         *         *         *         *

Leu Thr Arg Leu Tyr Ser Ile Cys Arg Asp Leu Leu Ser Arg Ser
TTGACCAGACTATACAGCATCTGCAGGGACTTACTATCCAGGAGC
 2300         *         *         *         *

Phe Leu Thr Leu Gln Leu Ile Tyr Gln Asn Leu Arg Asp Trp Leu
CTCCTGACCCTCCAACTCATCTACCAGAATCTCAGAGACTGGCTG
         *         *         *         *

Arg Leu Arg Thr Ala Phe Leu Gln Tyr Gly Cys Glu Trp Ile Gln
AGACTTAGAACAGCCTTCTTGCAATATGGGTGCGAGTGGATCCAA
    *     2400          *         *         *

Glu Ala Phe Gln Ala Ala Ala Arg Ala Thr Arg Glu Thr Leu Ala
GAAGCATTCCAGGCCGCCGCGAGGGCTACAAGAGAGACTCTTGCG
         *         *         *         *

Gly Ala Cyc Arg Gly Leu Trp Arg Val Leu Glu Arg Ile Gly Arg
GGCGCGTGCAGCGGCTTGTGGAGGGTATTGGAACGAATCGGGAGG
    *         *      2500         *         *

Gly Ile Leu Ala Val Pro Arg Arg Ile Arg Gln Gly Ala Glu Ile
CGAATACTCGCGGTTCCAAGAAGGATCAGACAGGCAGCAGAAATC
         *         *         *         *

Ala Leu Leu *** Gly Thr Ala Val Ser Ala Gly Arg Leu Tyr Glu
GCCCTCCTGTGAGGGACGGCAGTATCAGCAGGGAGACTTTATGAA
    *         *         *     2600          *

Tyr Ser Met Glu Gly Pro Ser Ser Arg Lys Gly Glu Lys Phe Val
TACTCCATGGAAGGACCCAGCAGCAGAAAGGGAGAAAAATTTGTA
         *         *         *         *

Gln Ala Thr Lys Tyr Gly
CAGGCAACAAAATATGGA
    *         *
```

<u>Gag sequence</u>

```
Met Gly Ala Arg Asn Ser Val Leu Arg Gly Lys Lys Ala Asp Glu
ATGGGCGCGAGAAACTCCGTCTTGAGAGGGAAAAAAGCAGATGAA
         *         *         *         *
Leu Glu Arg Ile Arg Leu Arg Pro Gly Gly Lys Lys Lys Tyr Arg
TTAGAAAGAATCAGGTTACGGCCCGGCGGAAAGAAAAAGTACAGG
    *         *         *         *         *
Leu Lys His Ile Val Trp Ala Ala Asn Lys Leu Asp Arg Phe Gly
CTAAAACATATTGTGTGGGCAGCGAATAAATTGGACAGATTCGGA
       100         *         *         *
Leu Ala Glu Ser Leu Leu Glu Ser Lys Glu Gly Cys Gln Lys Ile
TTAGCAGAGAGCCTGTTGGAGTCAAAAGAGGGTTGTCAAAAAATT
    *         *         *         *         *
Leu Thr Val Leu Asp Pro Met Val Pro Thr Gly Ser Glu Asn Leu
CTTACAGTTTTAGATCCAATGGTACCGACAGGTTCAGAAAATTTA
         *       200         *         *
Lys Ser Leu Phe Asn Thr Val Cys Val Ile Trp Cys Ile His Ala
AAAAGTCTTTTTAATACTGTCTGCGTCATTTGGTGCATACACGCA
    *         *         *         *         *
Glu Glu Lys Val Lys Asp Thr Glu Gly Ala Lys Gly Ile Val Arg
GAAGAGAAAGTGAAAGATACTGAAGGAGCAAAACAAATAGTGCGG
         *         *       300         *
Arg His Leu Val Ala Glu Thr Gly Thr Ala Glu Lys Met Pro Ser
AGACATCTAGTGGCAGAAACAGGAACTGCAGAGAAAATGCCAAGG
    *         *         *         *         *
Thr Ser Arg Pro Thr Ala Pro Ser Ser Glu Lys Gly Asn Asn Tyr
ACAAGTAGACCAACAGCACCATCTAGCGAGAAGGGAGGAAATTAC
         *         *         *       400
Pro Val Gln His Val Gly Gly Asn Tyr Thr His Ile Pro Leu Ser
CCAGTGCAACATGTAGGCGGCAACTACACCCATATACCGCTGAGT
    *         *         *         *         *
Pro Arg Thr Leu Asn Ala Trp Val Lys Leu Val Glu Glu Lys Lys
CCCCGAACCCTAAATGCCTGGGTAAAATTAGTAGAGGAAAAAAAG
         *         *         *         *
```

-continued

```
Phe Gly Ala Glu Val Val Pro Gly Phe Gln Ala Leu Ser Glu Gly
TTCGGGGCAGAAGTAGTGCCAGGATTTCAGGCACTCTCAGAAGGC
     500         *         *         *         *         *
Cys Thr Pro Tyr Asp Ile  Asn Gln Met Leu Asn Cys Val Gly Asp
TGCACGCCCTATGATATCAACCAAATGCTTAATTGTGTGGGCGAC
         *         *         *         *
His Gln Ala Ala Met Gln Ile  Ile  Arg Glu Ile  Ile  Asn Glu Glu
CATCAAGCAGCCATGCAGATAATCAGGGAGATTATCAATGAGGAA
                    600         *         *         *
Ala Ala Glu Trp Asp Val Gln His Pro Ile  Pro Gly Pro Leu Pro
GCAGCAGAATGGGATGTGCAACATCCAATACCAGGCCCCTTACCA
         *         *         *         *         *
Ala Gly Gln Leu Arg Glu Pro Arg Gly Ser Asp Ile  Ala Gly Thr
GCGGGGCAGCTTAGAGAGCCAAGGGGATCTGACATAGCAGGGAGA
         *         *         700         *         *
Thr Ser Thr Val Glu Glu Gln Ile  Gln Trp Met Phe Arg Pro Gln
ACAAGCACAGTAGAAGAACAGATCCAGTGGATGTTTAGGCCAGAA
Asn Pro Val Pro Val Gly Asn Ile  Tyr Arg Arg Trp Ile  Gln Ile
AATCCTGTACCAGTAGGAAACATCTATAGAAGATGGATCCAGATA
         *         *         *         800        *
Gly Leu Gln Lys Cys Val Arg Met Tyr Asn Pro Thr Asn Ile  Leu
GGATTGCAGAAGTGTGTCAGGATGTACAACCCGACCAACATCCTA
         *         *         *         *         *
Asp Ile  Lys Gln Gly Pro Lys Glu Pro Phe Gln Ser Tyr Val Asp
GACATAAAACAGGGACCAAAGGAGCCGTTCCAAAGCTATGTAGAT
         *         *         *         *         900
Arg Phe Tyr Lys Ser Leu Arg Ala Glu Gln Thr Asp Pro Ala Val
AGATTCTACAAAAGCTTGAGGGCAGAACAAACAGATCCAGCAGTG
         *         *         *         *         *
Lys Asn Trp Met Thr Gln Thr Leu Leu Val Gln Asn Ala Asn Pro
AAGAATTGGATGACCCAAACACTGCTAGTACAAAATGCCAACCCA
         *         *         *         *         *
Asp Cys Lys Leu Val Leu Lys Gly Leu Gly Met Asn Pro Thr Leu
GACTGTAAATTAGTGCTAAAAGGACTAGGGATGAACCCTACCTTA
         1000        *         *         *         *
Glu Glu Met Leu Thr Ala Cys Gln Gly Val Gly Gly Pro Gly Gln
GAAGAGATGCTGACCGCCTGTCAGGGGGTAGGTGGGCCAGGCGAG
         *         *         *         *
Lys Ala Arg Leu Met Ala Glu Ala Leu Lys Glu Val Ile  Gly Pro
AAAGCTAGATTAATGGCAGAGGCCCTGAAAGAGGTCATAGGACCT
         *         1100        *         *         *
Ala Pro Ile  Pro Phe Ala Ala Ala Gln Gln Arg Lys Ala Phe Phe
GCCCCTATCCCATTCGCAGCAGCCCAGCAGAGAAAGGCATTTAAA
         *         *         *         *         *
Cys Trp Asn Cys Gly Lys Glu Gly His Ser Ala Arg Gln Cys Arg
TGCTGGAACTGTGGAAAGGAAGGGCACTCGGCAAGACAATGCCGA
         *         *         1200        *         *
Ala Pro Arg Arg Gln Gly Cys Trp Lys Cys Gly Lys Pro Gly His
GCACCTAGAAGGCAGGGCTGCTGGAAGTGTGGTAAGCCAGGACAC
         *         *         *         *         *
Ile  Met Thr Asn Cys Pro Asp Arg Gln Ala Gly Phe Leu Gly Leu
ATCATGACAAACTGCCCAGATAGACAGGCAGGTTTTTTAGGACTG
         *         *         *         *         1300
Gly Pro Trp Gly Lys Lys Pro Arg Asn Phe Pro Val Ala Gln Val
GGCCCTTGGGGAAAGAAGCCCCGCAACTTCCCCCTGGCCCAAGTT
         *         *         *         *         *
Pro Gln Gly Leu Thr Pro Thr Ala Pro Pro Val Asp Pro Ala Val
CCGCAGGGGCTGACACCAACAGCACCCCCAGTGGATCCAGCAGTG
         *         *         *         *         *
Asp Leu Leu Glu Lys Tyr Met Gln Gln Gly Lys Arg Gln Arg Glu
GATCTACTGGAGAAATATATGCAGCAAGGGAAAAGACAGAGAGAG
         1400        *         *         *         *
Gln Arg Glu Arg Pro Tyr Lys Glu Val Thr Glu Asp Leu Leu His
CAGAGAGAGAGACCATACAAGGAAGTGACAGAGGACTTACTGCAC
         *         *         *         *         *
Leu Glu Gln Gly Glu Thr Pro Tyr Arg Gln Pro Pro Thr Glu Asp
CTCGAGCAGGGGGAGACACCATACAGGGAGCCACCAACAGAGGAC
         *         1500        *         *         *
Leu Leu His Leu Asn Ser Leu Phe Gly Lys Asp Gln
TTGCTGCACCTCAATTCTCTCTTTGGAAAAGACCAG
         *         *         *
```

Example 6

Peptide Sequences Encoded By The ENV and GAG genes

The following coding regions for antigenic peptides, identified for convenience only by the nucleotide numbers of Example 5, within the env and gag gene regions are of particular interest.

envl (1732–1809)

```
                        Arg Val Thr Ala Ile  Glu Lys Tyr
                        AGAGTCACTGCTATAGAGAAGTAG
```

```
Leu Gln Asp Gln Ala Arg Leu Asn Ser Trp Gly Cys Ala Phe Arg
CTACAGGACCAGGCGCGGCTAAATTCATGGGGATGTGCGTTTAGA
                                             1800
```

Gln Val Cys
CAAGTCTGC env2 (1912–1983)

```
                    Ser Lys Ser Leu Glu Gln Ala Gln
                    AGTAAAAGTTTAGAACAGGCACAA
```

```
Ile  Gln Gln Glu Lys Asn Met Tyr Glu Leu Gln Lys  Leu Asn Ser
ATTCAGCAAGAGAAAAATATGTATGAACTACAAAAATTAAATAGC
 1940.
```

Trp
TGG env3 (1482–1530)

```
Pro Thr Lys Glu Lys Arg Tyr Ser Ser Ala His Gly Arg His Thr Arg
CCTACAAAAGAAAAAAGATACTCCTCTGCTCACGGGAGACATACAAGA
              1500
``` env4 (55–129)

```
        Cys Thr Gln Tyr Val Thr Val Phe Tyr Gly Val Pro
        TGCACCCAATATTGAACTGTTTTCTATGGCGTACCC
```

```
Thr Trp Lys Asn Ala Thr Ile  Pro Leu Phe Cys Ala  Thr
ACGTGGAAAAATGCAACCATTCCCCTCTTTTGTGCAACC
            100
``` env5 (175–231)

```
                                        Asp Asp
                                        GATGAT
```

```
Tyr Gln Glu Ile  Thr Leu Asn Val Thr Glu Ala Phe Asp Ala  Trp
TATCAGGAAATAACTTTGAATGTAACAGAGGCTTTTGATGCATGG
                 200
```

Asn Asn
AATAAT env6 (274–330)

```
   Glu Thr Ser Ile  Lys Pro Cys Val Lys Leu Thr Pro Leu Cys
   GAGACATCAATAAAACCATGTGTGAAACTAACACCTTTATGT
                            300
```

Val Ala Met Lys Cys
GTAGCAATGAAATGC env7 (607–660)

```
                    Asn His Cys Asn Thr Ser Val Ile
                    AACCATTGCAACACATCAGTCATC
                    610
```

```
Thr Glu Ser Cys Asp Lys His Tyr Trp Asp
ACAGAATCATGTGACAAGCACTATTGGGAT
``` env8 (661–720)

```
                            Ala Ile  Arg Phe Arg
                            GCTATAAGGTTTAGA
```

-continued

Tyr Cys Ala Pro Pro Gly Tyr Ala Leu Leu Arg Cys Asn Asp Thr
TACTGTGCACCACCGGGTTATGCCCTATTAAGATGTAATGATACC
                              700 env9 (997–1044)

Lys Arg Pro Arg Gln Ala Trp Cys Trp Phe Lys Gly Lys
        AAAAGACCCAGACAAGCATGGTGCTGGTTCAAAGGCAAA
        1000

Trp Lys Asp
TGGAAAGAC env10 (1132–1215)

Lys Gly Ser Asp Pro Glu Val Ala Tyr Met Trp Thr Asn
        AAAGGCTCAGACCCAGAAGTAGCATACATGTGGACTAAC

Cys Arg Gly Glu Phe Leu Tyr Cys Asn Met Thr Trp Phe Leu Asn
TGCAGAGGAGAGTTTCTCTACTGCAACATGACTTGGTTCCTCAAT
                        1200 env11 (1237–1305)

Arg Asn Tyr Ala Pro Cys His Ile
                        CGCAATTATGCACCGTGCCATATA

Lys Gln Ile Ile Asn Thr Trp His Lys Val Gly Arg Asn Val Tyr
AAGCAAATAATTAACACATGGCATAAGGTAGGGAGAAATGTATAT
                                        1300 gag1 (991–1053)

Asp Cys Lys Leu Val Leu Lys Gly Leu Gly Met Asn Pro Thr Leu
GACTGTAAATTAGTGCTAAAAGGACTAGGGATGAACCCTACCTTA
        1000

Glu Glu Met Leu Thr Ala
GAAGAGATGCTGACCGCC

Of the foregoing peptides, env1, env2, env3 and gag1 are particularly contemplated for diagnostic purposes, and env4, env5, env6, env7, env8, env9, env10 and env11 are particularly contemplated as protecting agents. This invention fuirther relates to a peptide having common immunological properties with the peptide structure of the envelope glycoprotein of a virus of the HIV-2 class. In particular, the invention relates to peptides such as the peptide having either the formula XR--A-E-D-YL-DQ--L--WGC-----CZ or XA-E-D-YL-DZ, in which X and Z are OH or NH$_2$ or, to the extent that the immunological properties of the natural peptides lacking these groups shall not be essentially modified, the groups having from one to five amino acid residues, and each of the hyphens corresponding to an aminoacyl residue chosen from those which permit the conservation for the peptide characterized above of the immunological properties of either of the following peptide sequences, RVTAIEKYLQDQARLNSWGCAFRQVC or AIEKYLQDQ.

The invention further relates to the peptide having either the formula, X--E--Q-QQEKN-EL--L---Z or XQ-QQEKNZ, in which X and Z are OH or NH$_2$ or, to the extent that the immunological properties of the natural peptides lacking these groups shall not be essentially modified, the groups having from one to five amino acid residues, and each of the hyphens corresponding to an aminoacyl residue chosen from those which permit the conservation for the peptide characterized above of the immunological properties of either of the following peptide sequences: SLEQAQIQQEKNMYELQKLNSW or QIQQEKN.

The invention further relates to the peptide having either the formula XEL--YK-V-I-P-G-APTK-KR-----Z or XYK-V-I-P-G-APTK-KRZ, in which X and Z are OH or NH$_2$ or, to the extent that the immunological properties of the natural peptides lacking these groups shall not be essentially modified, the groups having from one to five amino acid residues, and each of the hyphens corresponding to an aminoacyl residue chosen from those which permit the conservation for the peptide characterized above of the immunological properties of either of the following peptide sequences: ELGDYKLVEITPIGFAPTKEKRYSSAH or YKLVEITPIGFAPTKEK.

The invention further relates to the peptide having either the formula X----VTV-YGVP-WK-AT--LPCA-Z or XVTV-YGVP-WK-ATZ, in which X and Z are OH or NH$_2$ or, to the extent that the immunological properties of the natural peptides lacking these groups shall not be essentially modified, the groups having from one to five amino acid residues, and each of the hyphens corresponding to an aminoacyl residue chosen from those which permit the conservation for the peptide characterized above of the immunological properties of one of the following peptide sequences: CTQYVTVFYGVPTWKNATIPLFCAT, V T V F Y G V P T W K N A T , EKLWVTVYYGVPVWKEATTTLFCAS, or VTVYYGVPVWKEAT. Preferably, this peptide has one of the following peptide sequences: C T Q Y V T V F Y G V P T W K N AT I P L F C AT, V T V F Y G V P T W K N A T , E K L W V T V Y Y G V P V W K E AT T T L F C A S , V T V Y Y G V P V W K E A T , EDLWVTVYYGVPVWKEATTTLFCAS, or DNL-WVTVYYGVPVWKEATTTLFCAS.

The invention further relates to peptide having either the formula X---QE--L-NVTE-F--W-NZ or XL-NVTE-FZ, in which X and Z are OH or $NH_2$ or, to the extent that the immunological properties of the natural peptides lacking these groups shall not be essentially modified, the groups having from one to five amino acid residues, and each of the hyphens corresponding to an aminoacyl residue chosen from those which permit the conservation for the peptide characterized above of the immunological properties of one of the following peptide sequences: DDYQEITL-NVTEAFDAWNN, L-NVTE, PNPQEVVLVNVTENFNMWKN, and LVNVTE. Preferably, this peptide has one of the following formulas: DDYQEITL-NVTEAFDAWNN, L-NVTEAF, PNPQEVVLVNVTENFNMWKN, LVNVTENF, PNPQEIELENVTEGFNMWKN, LENVTEGF, PNPQEIALENVTENFNMWKN, and LENVTENF.

The invention further relates to the peptide having either the formula XL---S-KPCVKLTPLCV--KZ, XKPCVKLT-PLCVZ or XS-KPCVKLTPLCVZ, in which X and Z are OH or $NH_2$ or, to the extent that the immunological properties of the natural peptides lacking these groups shall not be essentially modified, the groups having from one to five amino acid residues, and each of the hyphens corresponding to an aminoacyl residue chosen from those which permit the conservation for the peptide characterized above of the immunological properties of one of the following peptide sequences: ETSIKPCVKLTPLCVAMK, DQSLKPCVKLTPLCVSLK, KPCVKLTPLCV, and SLK-PCVKLTPLCV. Preferably, this peptide has one of the following formulas: ETSIKPCVKLTPLCVAMK, DQSLKPCVKLTPLCVSLK, DQSLKPCVKLTPLCVTLN, or PCVKLTPLC.

The invention further relates to a peptide having either of the following formulas: X---N-S-IT--C-Z or XN-S-ITZ, in which X and Z are OH or $NH_2$ or, to the extent that the immunological properties of the natural peptides lacking these groups shall not be essentially modified, the groups having from one to five amino acid residues, and each of the hyphens corresponding to an aminoacyl residue chosen from those which permit the conservation for the peptide characterized above of the immunological properties of one of the following peptide sequences: NHCNTSVITESCD, NTSVIT, TSCNTSVITQACP, or NTSAIT. Preferably, this peptide has one of the following formulas: NHCNTSVITESCD, NTSVIT, TSCNTSVITQACP, INCNTSVITQACP, INCNTSAITQACP, or NTSAIT.

The invention further relates to a peptide having the formula XYC-P-G-A-L-C-N-TZ, in which X and Z are OH or NH2 or, to the extent that the immunological properties of the natural peptides lacking these groups shall not be essentially modified, the groups having from one to five amino acid residues, and each of the hyphens corresponding to an aminoacyl residue chosen from those which permit the conservation for the peptide characterized above of the immunological properties of either of the following peptide sequences: YCAPPGYALLRC-NDT or YCAPAG-FAILKCNNKT. Preferably, this peptide has one of the following formulas: YCAPPGYALLRC-NDT, YCAPAGFAILKCNNKT, YCAPAGFAILKCNDKK, or YCAPAGFAILKCRDKK.

Moreover, the invention relates to a peptide having the formula X------A-C------W--Z, in which X and Z are OH or NH2 or, to the extent that the immunological properties of the natural peptides lacking these groups shall not be essentially modified, the groups having from one to five amino acid residues, and each of the hyphens corresponding to an aminoacyl residue chosen from those which permit the conservation for the peptide characterized above of the immunological properties of either of the following peptide sequences: NKRPRQAWCWFKG-KWKD or N--MRQAHCNISRAKWNA. Preferably, this peptide has one of the following formulas: NKRPRQAWCWFKG-KWKT, N--MRQAHCNISRAKWNA, D--IRRAYCTINETEWDK, or I--IGQAHCNISRAQWSK.

The invention also relates to a peptide having either of the following formulas X-G-DPE------NC-GEF-YCN-----NZ or XNC-GEF-YCNZ, in which X and Z are OH or $NH_2$ or, to the extent that the immunological properties of the natural peptides lacking these groups shall not be essentially modified, the groups having from one to five amino acid residues, and each of the hyphens corresponding to an aminoacyl residue chosen from those which permit the conservation for the peptide characterized above of the immunological properties of one of the following peptide sequences: KGSDPEVAYMWTNCRGEFLYCNMTWFLN, N C R G E F L Y C N , -GGDPEIVTHSFNCGGEFFYCNSTQLFN, or NCGGEFFYCN. Preferably, this peptide has one of the following formulas: KGSDPEVAYMWTNCRGEFLYCNMTWFLN, N C R G E F L Y C N , -GGDPEIVTHSFNCGGEFFYCNSTQLFN, N C G G E F F Y C N , -GGDPEITTHSFNCRGEFFYCNTSKLFN, NCRGEFFYCN, or -GGDPEITTHSFNCGGEFFYCNTSGLFN.

The invention further relates to a peptide having either of the following formulas: X-----C-IKQ-I------G---YZ or XC-IKQ-IZ, in which X and Z are OH or $NH_2$ or, to the extent that the immunological properties of the natural peptides lacking these groups shall not be essentially modified, the groups having from one to five amino acid residues, and each of the hyphens corresponding to an aminoacyl residue chosen from those which permit the conservation for the peptide characterized above of the immunological properties of one of the following peptide sequences: RNYAPCHIKQIINTWHKVGRNVY, CHIKQII, TITLPCRIKQFINMWQEVGKAMY, or CRIKQFI. Preferably, this peptide has one of the following formulas: RNYAPCHIKQIINTWHKVGRNVY, CHIKQII, TITLPCRIKQFINMWQEVGKAMY, CRIKQFI, SITLPCRIKQIINMWQKTCKAMY, CRIKQII, or NITLQCRIKQIIKMVAGR-KAIY.

The invention further relates to a peptide, gag1, having the following formula: XNCKLVLKGLGMNPTLEEMLTAZ, in which X and Z are OH or $NH_2$ or, to the extent that the immunological properties of the natural peptides lacking these groups shall not be essentially modified, the groups having from one to five amino acid residues, and each of the hyphens corresponding to an aminoacyl residue chosen from those which permit the conservation for the peptide characterized above of the immunological properties of the following peptide sequence: XNCKLVLKGLGMNPTLEEMLTAZ. These peptides have been selected in part because of their sequence homology to certain of the envelope and gag protein products of other of the retroviruses in the H:V group. For vaccinating purposes, the fore going peptides may be coupled to a carrier protein by utilizing suitable and well known techniques to enhance the host's immune response.

Adjuvants such as calcium phosphate or alum hydroxide may also be added. The foregoing peptides can be synthesized by conventional protein synthesis techniques, such as that of Merrifield.

It will be apparent to those skilled in the art that various modifications and variations can be made in the processes and products of the present invention. Thus, it is intended that the present application cover the modifications and variations of this invention provided they come within the scope of the appended claims and their equivalents. For convenience in interpreting the following claims, the following table sets forth the correspondence between codon codes and amino acids and the correspondence between three-letter and one-letter amino acid symbols.

erties of the peptide having the terminal group shall not be essentially modified from the peptide lacking the terminal group, and wherein each of the hyphens corresponds to an aminoacyl residue chosen from among those which permit the conservation of the immunological properties of either of the following peptide sequences:

RVTAIEKYLQDQARLNSWGCAFRQVC or

AIEKYLQDQ.

2. A purified nucleic acid encoding a peptide comprising an amino acid sequence of either of the following formulas:

X--E--Q-QQEKN--EL--L---Z

| \2 | | DNA CODON | | | | AMINO ACID 3 LET. | | | | AMINO ACID 1 LET. | | |
|---|---|---|---|---|---|---|---|---|---|---|---|---|
| 1 | 3\ T | C | A | G | T | C | A | G | T | C | A | G |
| T | T TTT | TCT | TAT | TGT | PHE | SER | TYR | CYS | F | S | Y | C |
|   | C TTC | TCC | TAC | TGC | PHE | SER | TYR | CYS | F | S | Y | C |
|   | A TTA | TCA | TAA | TCA | LEU | SER | *** | *** | L | S | * | * |
|   | G TTG | TCG | TAG | TCG | LEU | SER | *** | TRP | L | S | * | W |
| C | T CTT | CCT | CAT | CGT | LEU | PRO | HIS | ARG | L | P | H | R |
|   | C CTC | CCC | CAC | CGC | LEU | PRO | HIS | ARG | L | P | H | R |
|   | A CTA | CCA | CAA | CGA | LEU | PRO | GLN | ARG | L | P | O | R |
|   | G CTG | CCG | CAG | CCG | LEU | PRO | GLN | ARG | L | P | O | R |
| A | T ATT | ACT | AAT | AGT | ILE | THR | ASN | SER | I | T | N | S |
|   | C ATC | ACC | AAC | AGC | ILE | THR | ASN | SER | I | T | N | S |
|   | A ATA | ACA | AAA | AGA | ILE | THR | LYS | ARG | I | T | K | R |
|   | G ATG | ACG | AAG | AGG | MET | THR | LYS | ARG | M | T | K | R |
| G | T GTT | GCT | GAT | GGT | VAL | ALA | ASP | GLY | V | A | D | G |
|   | C GTC | GCC | GAC | GGC | VAL | ALA | ASP | GLY | V | A | D | G |
|   | A GTA | GCA | GAA | GGA | VAL | ALA | GLU | GLY | Y | A | E | G |
|   | G GTG | CCG | GAG | GCG | VAL | ALA | GLU | GLY | V | A | E | G |

| 3 Letter | 1 Letter | CODONS | | | | | |
|---|---|---|---|---|---|---|---|
| ALA | A | GCT | GCC | GCA | GCG | | |
| ARG | R | CGT | CGC | CGA | CGC | AGA | AGG |
| ASN | N | AAT | AAC | | | | |
| ASP | D | GAT | GAC | | | | |
| CYS | C | TGT | TCC | | | | |
| GLN | O | CAA | CAG | | | | |
| GLU | E | GAA | CAG | | | | |
| GLY | G | GGT | GGC | GGA | GGG | | |
| HIS | H | CAT | CAC | | | | |
| ILE | I | ATT | ATC | ATA | | | |
| LEU | L | CTT | CTC | CTA | CTG | TTA | TTG |
| LYS | K | AAA | AAG | | | | |
| MET | M | ATG | | | | | |
| PHE | F | TTT | TTC | | | | |
| PRO | P | CCT | CCC | CCA | CCG | | |
| SER | S | TCT | TCC | TCA | TCG | AGT | AGC |
| THR | T | ACT | ACC | ACA | ACG | | |
| TRP | W | TGG | | | | | |
| TYR | Y | TAT | TAC | | | | |
| VAL | V | GTT | GTC | GTA | GTG | | |
| *** | * | TAA | TAG | TGA | | | |

What is claimed is:

1. A purified nucleic acid encoding a peptide comprising an amino acid sequence of either of the following formulas:

XR--A-E-D-YL-DQ--L--WGC-----CZ or

XA-E-D-YL-DZ, wherein X and Z are OH or NH$_2$ or at least one of X and Z comprises a terminal group comprising from one to five amino acid residues, provided that the immunological properties of the peptide having the terminal group shall not be essentially modified from the peptide lacking the terminal group, and wherein each of the hyphens correspond to an aminoacyl residue chosen from those which permit the conservation of the immunological properties of either of the following peptide sequences:

or

XQ-QQEKNZ, wherein X and Z are OH or NH$_2$, or at least one of X and Z comprises a terminal group comprising from one to five amino acid residues, provided that the immunological properties of the peptide having the terminal group shall not be essentially modified from the peptide lacking the terminal group, and wherein each of the hyphens correspond to an aminoacyl residue chosen from those which permit the conservation of the immunological properties of either of the following peptide sequences:

SLEQAQIQQEKNMYELQKLNSW or

QIQQEKN.

3. A purified nucleic acid encoding a peptide comprising an amino acid sequence of either of the following formulas:

XEL--YK-V-I-P-G-APTK-KR-----Z or

XYK-V-I-P-G-APTK-KRZ, wherein X and Z are OH or NH$_2$, or at least one of X and Z comprises a terminal group comprising from one to five amino acid residues, provided that the immunological properties of the peptide having the terminal group shall not be essentially modified from the peptide lacking the terminal group, and wherein each of the hyphens correspond to an aminoacyl residue chosen from those which permit the conservation of the immunological properties of either of the following peptide sequences:

ELGDYKLVEITPIGFAPTKEKRYSSAH or

YKLVEITPIGFAPTKEK.

4. A purified nucleic acid encoding a peptide comprising an amino acid sequence of either of the following formulas:

X----VTV-YGVP-WK-AT--LPCA-Z or

XVTV-YGVP-WK-ATZ, wherein X and Z are OH or NH$_2$, or at least one of X and Z comprises a terminal group comprising from one to five amino acid residues, provided that the immunological properties of the peptide having the terminal group shall not be essentially modified from the peptide lacking the terminal group, and wherein each of the hyphens correspond to an aminoacyl residue chosen from those which permit the conservation of the immunological properties of one of the following peptide sequences:

CTQYVTVFYGVPTWKNATIPLFCAT,

VTVFYGVPTWKNAT,

EKLWVTVYYGVPVWKEATTTLFCAS, or

VTVYYGVPVWKEAT.

5. The nucleic acid of claim 4, wherein the the amino acid sequence has one of the following formulas:

CTQYVTVFYGVPTWKNATIPLFCAT,

VTVFYGVPTWKNAT,

EKLWVTVYYGVPVWKEATTTLFCAS,

VTVYYGVPVWKEAT,

EDLWVTVYYGVPVWKEATTTLFCAS, or

DNLWVTVYYGVPVWKEATTTLFCAS.

6. A purified nucleic acid encoding a peptide comprising an amino acid sequence of either of the following formulas:

X---QE--L-NVTE-F--W-NZ or

XL-NVTE-FZ, wherein X and Z are OH or NH$_2$, or at least one of X and Z comprises a terminal group comprising from one to five amino acid residues, provided that the immunological properties of the peptide having the terminal group shall not be essentially modified from the peptide lacking the terminal group, and wherein each of the hyphens correspond to an aminoacyl residue chosen from those which permit the conservation of the immunological properties of one of the following peptide sequences:

DDYQEITL-NVTEAFDAWNN,

L-NVTE,

PNPQEVVLVNVTENFNMWKN, or

LVNVTE.

7. The nucleic acid of claim 6, wherein the nucleic acid encodes an amino acid sequence of one of the following formulas:

DDYQEITL-NVTEAFDAWNN,

L-NVTEAF,

PNPQEVVLVNVTENFNMWKN,

LVNVTENF,

PNPQEIELENVTEGFNMWKN,

LENVTEGF,

PNPQEIALENVTENFNMWKN, or

LENVTENF.

8. A purified nucleic acid encoding a peptide comprising an amino acid sequence of one of the following formulas:

XL---S-KPCVKLTPLCV--KZ,

XKPCVKLTPLCVZ, or

XS-KPCVKLTPLCVZ, wherein X and Z are OH or NH$_2$, or at least one of X and Z comprises a terminal group comprising from one to five amino acid residues, provided that the immunological properties of the peptide having the terminal group shall not be essentially modified from the peptide lacking the terminal group, and wherein each of the hyphens correspond to an aminoacyl residue chosen from those which permit the conservation of the immunological properties of one of the following peptide sequences:

ETSIKPCVKLTPLCVAMK,

DQSLKPCVKLTPLCVSLK,

KPCVKLTPLCV, or

SLKPCVKLTPLCV.

9. The nucleic acid of claim 8, wherein the nucleic acid encodes an amino acid sequence having one of the following formulas:

ETSIKPCVKLTPLCVAMK,

DQSLKPCVKLTPLCVSLK,

DQSLKPCVKLTPLCVTLN, or

PCVKLTPLC.

10. A purified nucleic acid encoding a peptide comprising an amino acid sequence of one of the following formulas:

X---N-S-IT--C-Z or

XN-S-ITZ, wherein X and Z are OH or $NH_2$, or at least one of X and Z comprises a terminal group comprising from one to five amino acid residues, provided that the immunological properties of the peptide having the terminal group shall not be essentially modified from the peptide lacking the terminal group, and wherein each of the hyphens correspond to an aminoacyl residue chosen from those which permit the conservation of the immunological properties of one of the following peptide sequences:

NHCNTSVITESCD,

NTSVIT,

TSCNTSVITQACP, or

NTSAIT.

11. The nucleic acid of claim 10, wherein the nucleic acid encodes a peptide comprising an amino acid sequence of one of the following formulas:

NHCNTSVITESCD,

NTSVIT,

TSCNTSVITQACP,

INCNTSVITQACP,

INCNTSAITQACP, or

NTSAIT.

12. A purified nucleic acid encoding a peptide comprising an amino acid sequence of the following formula:

XYC-P-G-A-L-C-N-TZ, wherein X and Z are OH or $NH_2$, or at least one of X and Z comprises a terminal group comprising from one to five amino acid residues, provided that the immunological properties of the peptide having the terminal group shall not be essentially modified from the peptide lacking the terminal group, and wherein each of the hyphens correspond to an aminoacyl residue chosen from those which permit the conservation of the immunological properties of either of the following peptide sequences:

YCAPPGYALLRC-NDT or

YCAPAGFAILKCNNKT.

13. The nucleic acid of claim 12, wherein the nucleic acid encodes a peptide comprising an amino acid sequence of one of the following formulas:

YCAPPGYALLRC-NDT,

YCAPAGFAILKCNNKT,

YCAPAGFAILKCNDKK, or

YCAPAGFAILKCRDKK.

14. A purified nucleic acid encoding a peptide comprising an amino acid sequence of the following formula:

X----A-C------W--Z, wherein X and Z are OH or $NH_2$, or at least one of X and Z comprises a terminal group comprising from one to five amino acid residues, provided that the immunological properties of the peptide having the terminal group shall not be essentially modified from the peptide lacking the terminal group, and wherein each of the hyphens correspond to an aminoacyl residue chosen from those which permit the conservation of the immunological properties of one of the following peptide sequences:

NKRPRQAWCWFKG-KWKD or

N--MRQAHCNISRAKWNA.

15. The nucleic acid of claim 14, wherein the nucleic acid encodes a peptide comprising an amino acid sequence of one of the following formulas:

NKRPRQAWCWFKG-KWKT,

N--MRQAHCNISRAKWNA,

D--IRRAYCTINETEWDK, or

I--IGQAHCNISRAQWSK.

16. A purified nucleic acid encoding a peptide comprising an amino acid sequence of one of the following formulas:

X-G-DPE------NC-GEF-YCN-----NZ or

XNC-GEF-YCNZ, wherein X and Z are OH or $NH_2$, or at least one of X and Z comprises a terminal group comprising from one to five amino acid residues, provided that the immunological properties of the peptide having the terminal group shall not be essentially modified from the peptide lacking the terminal group, and wherein each of the hyphens correspond to an aminoacyl residue chosen from those which permit the conservation of the immunological properties of one of the following peptide sequences:

KGSDPEVAYMWTNCRGEFLYCNMTWFLN,

NCRGEFLYCN,

-GGDPEIVTHSFNCGGEFFYCNSTQLFN, or

NCGGEFFYCN.

17. The nucleic acid of claim 16, wherein the nucleic acid encodes a peptide of one of the following formulas:

KGSDPEVAYMWTNCRGEFLYCNMTWFLN,

NCRGEFLYCN,

-GGDPEIVTHSFNCGGEFFYCNSTQLFN,

NCGGEFFYCN,

-GGDPEITTHSFNCRGEFFYCNTSKLFN,

NCRGEFFYCN, or

-GGDPEITTHSFNCGGEFFYCNTSGLFN.

18. A purified nucleic acid encoding a peptide comprising an amino acid sequence of one of the following formulas:

X-----C-IKQ-I------G---YZ or

XC-IKQ-IZ, wherein X and Z are OH or NH$_2$, or at least one of X and Z comprises a terminal group comprising from one to five amino acid residues, provided that the immunological properties of the peptide having the terminal group shall not be essentially modified from the peptide lacking the terminal group, and wherein each of the hyphens correspond to an aminoacyl residue chosen from those which permit the conservation of the immunological properties of one of the following peptide sequences:

RNYAPCHIKQIINTWHKVGRNVY,

CHIKQII,

TITLPCRIKQFINMWQEVGKAMY, or

CRIKQFI.

19. The nucleic acid of claim 18, wherein the nucleic acid encodes a peptide comprising an amino acid sequence of one of the following formulas:

RNYAPCHIKQIINTWHKVGRNVY,

CHIKQII,

TITLPCRIKQFINMWQEVGKAMY,

CRIKQFI,

SITLPCRIKQIINMWQKTCKAMY,

CRIKQII, or

NITLQCRIKQIIKMVAGR-KAIY.

20. A purified nucleic acid encoding a peptide, gag1, having the following formula: XNCKLVLKGLGMNPTLEEMLTAZ, in which X and Z are OH or NH$_2$ or, to the extent that the immunological properties of the natural peptides lacking these groups shall not be essentially modified, the groups having from one to five amino acid residues, and each of the hyphens corresponding to an aminoacyl residue chosen from those which permit the conservation for the peptide characterized above of the immunological properties of the following peptide sequence:

XNCKLVLKGLGMNPTLEEMLTAZ.

21. A method for detecting the presence or absence of Human Immunodeficiency Virus Type 2 (HIV-2) comprising:
  (1) contacting a sample suspected of containing viral genetic material of HIV-2 with at least one nucleotide probe, and
  (2) detecting hybridization between the nucleotide probe and the viral genetic material in the sample,
  wherein said nucleotide probe is complementary to the full-length sequence of the purified nucleic acid selected from the group consisting of the purified nucleic acids of claims 84–103.

* * * * *